US007557186B2

(12) United States Patent
Tuli

(10) Patent No.: US 7,557,186 B2
(45) Date of Patent: Jul. 7, 2009

(54) CHIMERIC CRYLE δ ENDOTOXIN AND METHODS OF CONTROLLING INSECTS

(75) Inventor: Rakesh Tuli, Uttar Pradesh (IN)

(73) Assignee: Council of Scientific & Industrial Research (IN)

(*) Notice: Subject to any disclaimer, the term of this patent is extended or adjusted under 35 U.S.C. 154(b) by 159 days.

(21) Appl. No.: 11/062,225

(22) Filed: Feb. 18, 2005

(65) Prior Publication Data
US 2005/0272060 A1 Dec. 8, 2005

Related U.S. Application Data

(62) Division of application No. 10/107,581, filed on Mar. 27, 2002, now Pat. No. 7,053,266.

(51) Int. Cl.
*C07K 14/325* (2006.01)
(52) U.S. Cl. .................................... 530/350
(58) Field of Classification Search ............... None
See application file for complete search history.

(56) References Cited

U.S. PATENT DOCUMENTS

| 4,448,885 | A | 5/1984 | Schnepf et al. |
| 4,467,036 | A | 8/1984 | Schnepf et al. |
| 4,797,276 | A | 1/1989 | Herrnstadt et al. |
| 4,849,217 | A | 7/1989 | Soares et al. |
| 4,853,331 | A | 8/1989 | Herrnstadt et al. |
| 4,918,006 | A | 4/1990 | Ellar et al. |
| 4,948,734 | A | 8/1990 | Edwards et al. |
| 5,055,294 | A | 10/1991 | Gilroy |
| 5,128,130 | A | 7/1992 | Gilroy et al. |
| 5,135,867 | A | 8/1992 | Payne et al. |
| 5,151,363 | A | 9/1992 | Payne |
| 5,208,017 | A | 5/1993 | Bradfisch et al. |

FOREIGN PATENT DOCUMENTS

WO    WO 95/06730    *    3/1995

OTHER PUBLICATIONS de Maagd et al, 1999, Appl. Environ. Microbiol. 65:4369-4374.*
Tounsi et al, 2003, J. Appl. Microbiol. 95:23-28.*
Angsuthanasombat et al, 2001, J. Biochem. Mol. Biol. 34:402-407.*
Aaronson et al, 2001, FEMS Microbiol. Lett. 195:1-8.*
de Maagd et al, 2001, Trends Genet. 17:193-199.*
Guo et al, 2004, Proc. Natl. Acad. Sci. USA 101: 9205-9210.*
Bai, et al., "Activity of Insecticidal Crystal Proteins and Strains of *Bacillus thuringiensis* against *Spodoptera exempta* (Walker)", Journal of Invertebrate Pathology, 62, pp. 211-215 (1993).
Barton et al., "*Bacillus thuringiensis* δ-Endotoxin Expressed in Transgenic *Nicotiana tabacum* Provides Resistance to Lepidoperan Insects", Plant Physiology, 85, pp. 1103-1109 (1987).
Beegle, "Use of Entomogenous Bacteria in Agroecosystems", Developments in Industrial Biology, vol. 20, pp. 97-104 (1978).
Bietlot, et al., "Facile preparation and characterization of the toxin from *Bacillus thuringiensis* var. *kurstaki*", Biochem. J., 260, pp. 87-91 (1989).
Bosch, et al., "Recombinant *Bacillus thuringiensis* Crystal Proteins with New Properties: Possibilities for Resistance Management", Bio/Technology, vol. 12, pp. 915-918, Sep. (1994).
Bulla, et al., "Ultrastructure, Physiology, and Biochemistry of *Bacillus Thuringiensis*", CRC Crit. Rev. Microbiol., 8, pp. 147-204, Oct. (1980).
Chandra, et al., "Amino acid substitution in α-helix of Cryl Ac δ-endotoxin of *Bacillus thuringiensis* leads to enhanced toxicity to *Helicoverpa armigera* Hubner", FEBS Letters, 458, pp. 175-179 (1999).
Choma, et al., "Unusual proteolysis of the protoxin and toxin from *Bacillus thuringiensis* Structural implications", Eur. J. Biochem., 189, pp. 523-527 (1990).
Couch, "Mosquito Pathogenicity of *Bacillus thuringiensis* var. *israelensis*", Development in Industrial Microbiology, 22, pp. 617-676 (1980).
Crickmore, et al., "Revision of the Nomenclature for the *Bacillus thuringiensis* Pesticidal Crystal Proteins", Microbiol. and Molecular Biology Reviews, pp. 807-813, Sep. (1998).
Feitelson, "The *Bacillus thuringiensis* Family Tree", L. kim ed. Advanced engineered pesticides, Marcel Dekker, Inc. pp. 63-71 (1993).
Feitelson, et al., "*Bacillus thuringiensis*: Insects and Beyond", Bio/Tech 10, pp. 271-275, (1992).
Fischoff, et al., "Insect Tolerant Transgenic Tomato Plants", Bio/Tech, 5, pp. 807-813 (1987).
Grochulsky et al., "*Bacillus thuringiensis* CrylA(a) Insecticidal Toxin: Crystal Structure and Channel Formation", J. Mol. Biol., 254, pp. 447-464 (1995).
Hofte, et al., "Structural and functional analysis of a cloned delta endotoxin of *Bacillus thuringiensis berliner* 1715", Eur. J. Biochem., 161, 273-280 (1986).
Honee, et al., "A Translation Fusion Product of Two Different Insecticidal Crystal Protein Genes of *Bacillus thuringiensis* Exhibits and Enlarged Insecticidal Spectrum", Applied and Environmental Microbiology, vol. 56, No. 3, pp. 823-825, Mar. (1990).
Honee, et al., "The C-terminal domain of the toxic fragment of a *Bacillus thuringiensis* crystal protein determines receptor binding", Molecular Microbiology, 5(11), pp. 2799-2806 (1991).
Kalman, et al., "Cloning of a Novel cryIC-Type Gene from a Strain of *Baciluus thuringiensis* subsp. *Galleriae*", Applied and Environmental Microbiology, vol. 59, No. 4, pp. 1131-1137, Apr. (1993).
Keller, et al., "Digestion of δ-Endotoxin by Gut Proteases may Explain Reduced Sensitivity of Advanced Instar Larvae of *Spodoptera littoralis* to CryIC", Insect Biochem. Molec., vol. 26, No. 4, pp. 365-373 (1996).

(Continued)

*Primary Examiner*—Anne R Kubelik
(74) *Attorney, Agent, or Firm*—Fish & Richardson P.C.

(57) ABSTRACT

The present invention relates to a chimeric δ endotoxin protein Cry 1E of SEQ ID No. 1 with extraordinarily high insecticidal property and a chimera gene of SEQ ID No. 2 encoding the said chimeric protein, and also a method of treating insect infested plants using said chimera protein.

1 Claim, 10 Drawing Sheets

OTHER PUBLICATIONS

Li, et al., "Crystal structure of insecticidal δ-endotoxin from *Bacillus thuringiensis* at 2.5 Å resolution", Nature, vol. 353, pp. 815-821, Oct. (1991).

Masson, et al., "Insecticidal Properties of a Crystal Protein Gene Product Isolated from *Bacillus thuringiensis* subsp. *kenyae*", Applied and Environmental Microbiology, vol. 58, No. 2, Feb. (1992).

Mazier, et al., "The cryic gene from *Bacillus thuringiensis* provides protection against *Spodoptera littoralis* in young transgenic plants", Plant Science, vol. 127, pp. 179-190 (1997).

Rang et al., "Interaction between Functional Domains of *Bacillus thuringiensis* Insecticidal Crystal Proteins", Applied and Environmental Microbiology, vol. 64, No. 7, pp. 2918-2925, Jul. (1999).

Schnepf, et al., "*Bacillus thuringiensis* and Its Pesticidal Crystal Proteins", Microbiology and Molecular Biology Reviews, vol. 62, No. 3, pp. 775-806, Sep. (1998).

Strizhov, et al. "A synthetic cryIC gene, encoding a *Bacillus thuringiensis* δ-endotoxin, confers *Spodoptera* resistance in alfalfa and tobacco", Proc. Natl. Acad. Sci., USA, vol. 93, pp. 15012-15017, Dec. (1996).

Van der Salm, et al., "Insect Resistance of transgenic plants that express modified *Bacillus thuringiensis* cryIA(b) and cryIC genes: a resistance management strategy", Plant Molecular Biology, 26, pp. 51-59 (1994).

Vaeck, et al., "Transgenic plants protected from insect attack", Nature, vol. 328, pp. 33-37, (1987).

Von Tersch et al., "Insecticidal Toxins from *Bacillus thuringiensis* subsp. *kenyae*: Gene Cloning and Characterization and Comparison with *B. thuringiensis* subsp. *kurstaki* CryIA(c) Toxins," Applied and Environmental Microbiology, vol. 57, No. 2, pp. 349-358 (Feb. 1991).

* cited by examiner

CRYAA1 (SEQ ID NO:3) MDNNPNINECIPYNCLSNPEVEVLGGE RIETGYTPI DISLSLTQFLLSEF
CRYAA4 (SEQ ID NO:4) MDNNPNINECIPYNCLSNPEVEVLGGE-RIETGYTPI DISLSLTQFLLSEF
CRYAA5 (SEQ ID NO:5) MDNNPNINECIPYNCLSNPEVEVLGGE RIETGYTPI DISLSLTQFLLSEF
CRYAA6 (SEQ ID NO:6) MDNNPNINECIPYNCLSNPEVEVLGGERIETGYTP DISLSLTQFLLSEF
CRYAA2 (SEQ ID NO:7) MDNNPNINECIPYNCLSNPEVEVLGGERIETGYTPI-DISLSLTQFLLSEF
CRYAA3 (SEQ ID NO:8) MDNNPNINECIPYNCLSNPEVEVLGGERIETGYTPI DISLSLTQFLLSEF

CRYAA1 VPGAGFVLGLVDIIWGIFGPSQWDAFPVQIEQL I NQRIEEFARNQAISRL
CRYAA4 VPGAGFVLGLVDIIWGIFGPSQWDAFPVQIEQL I-NQRIEEFARNQAISRL
CRYAA5 VPGAGFVLGLVDIIWGIFGPSQWDAFLVQIEQL I NQRIEEFARNQAISRL
CRYAA6 VPGAGFVLGLVDIIWGIFGPSQWDAFLVQIEQL I NQRIEEFARNQAISRL
CRYAA2 VPGAGFVLGLVDIIWGIFGPSQWDAFLVQIEQL-T NQRIEEFARNQAISRL
CRYAA3 VPGAGFVLGLVDIIWGIFGPSQWDAFLVQIEQL I NQRIEEFARNQAISRL

CRYAA1 EGLSNLYQIYAESFREWEADPTNPALREEMRI Q FNDMNSALTTAIPLLAV
CRYAA4 EGLSNLYQIYAESFREWEADPTNPALREEMRI Q-FNDMNSALTTAIPLLAV
CRYAA5 EGLSNLYQIYAESFREWEADPTNPALREEMRI Q FNDMNSALTTAIPLLAV
CRYAA6 EGLSNLYQIYAESFREWEADPTNPALREEMRI Q FNDMNSALTTAIPLLAV
CRYAA2 EGLSNLYQIYAESFREWEADPTNPALREEMRI Q FNDMNSALTTAIPLFAV
CRYAA3 EGLSNLYQIYAESFREWEADPTNPALREEMRI-Q FNDMNSALTTAIPLFAV

FIG. 7A

CRYAA1 QNYQVPLLSVYVQAANLHLSVLRDVSVFGQRWG FDAATINSRYNDLTRLI
CRYAA4 QNYQVPLLSVYVQAANLHLSVLRDVSVFGQRWG-FDAATINSRYNDLTRLI
CRYAA5 QNYQVPLLSVYVQAANLHLSVLRDVSVFGQRWG FDAATINSRYNDLTRLI
CRYAA6 QNYQVPLLSVYVQAANLHLSVLRDVSVFGQRWG FDAATINSRYNDLTRLI
CRYAA2 QNYQVPLLSVYVQAANLHLSVLRDVSVFGQRWG-FDAATINSRYNPLTRLI
CRYAA3 QNYQVPLLSVYVQAANLHLSVLRDVSVFGQRWG FDAATINSRYNDLTRLI

CRYAA1 GNYTDYAVRWYNTGLERVWGPDSRDWVRYNQFR R ELTLTVLDIVALFSNY
CRYAA4 GNYTDYAVRWYNTGLERVWGPDSRDWVRYNQFR-R ELTLTVLDIVALFSNY
CRYAA5 GNYTDYAVRWYNTGLERVWGPDSRDWVRYNQFR R ELTLTVLDIVALFSNY
CRYAA6 GNYTDYAVRWYNTGLERVWGPDSRDWVRYNQFR R ELTLTVLDWALFSNY
CRYAA2 GNYTDYAVRWYNTGLERVWGPDSRDWVRYNQFR R-ELTLTVLDIVALFSNY
CRYAA3 GNYTDYAVRWYNTGLERVWGPDSRDWVRYNQFR R ELTLTVLDWALFSNY

CRYAA1 DSRRYPIRTVSQLTREIYTNPVLENFDGSFRGM A QRIEQNIRQPHLMDIL
CRYAA4 DSRRYPIRTVSQLTREIYTNPVLENFDGSFRGM A-QRIEQNIRQPHLMDIL
CRYAA5 DSRRYPIRTVSQLTREIYTNPVLENFDGSFRGM A-QRIEQNIRQPHLMDIL
CRYAA6 DSRRYPIRTVSQLTREIYTNPVLENFDGSFRGM A QRIEQNIRQPHLMDIL
CRYAA2 DSRRYPIRTVSQLTREIYTNPVLENFDGSFRGM A QRIEQNIRQPHLMDIL
CRYAA3 DSRRYPIRTVSQLTREIYTNPVLENFDGSFRGM-A QRIEQNIRQPHLMDIL

FIG. 7B

CRYAA1 NSITIYTDVHRGFNYWSGHQITASPVGFSGPEF AFPLFGNAGNAAPPVLV
CRYAA4 NSITIYTDVHRGFNYWSGHQITASPVGFSGPEF-AFPLFGNAGNAAPPVLV
CRYAA5 NSITIYTDVHRGFNYWSGHQITASPVGFSGPEF AFPLFGNAGNAAPPVLV
CRYAA6 NSITIYTDVHRGFNYWSGHQITASPVGFSGPEF AFPLFGNAGNAAPPVLV
CRYAA2 NRITIYTDVHRGFNYWSGHQITASPVGFSGPEF-AFPLFGNAGNAAPPVLV
CRYAA3 NSITIYTDVHRGFNYWSGHQITASPVGFSGPEF AFPLFGNAGNAAPPVLV

CRYAA1 SLTGLGIFRTLSSPLYRRIILGSGPNNQELFV L DGTEFSFASLTTNLPST
CRYAA4 SLTGLGIFRTLSSPLYRRIILGSGPNNQELFV L-DGTEFSFASLTTNLPST
CRYAA5 SLTGLGIFRTLSSPLYRRIILGSGPNNQELFV L DGTEFSFASLTTNLPST
CRYAA6 SLTGLGIFRTLSSPLYRRIILGSGPNNQELFV L DGTEFSFASLTTNLPST
CRYAA2 SLTGLGIFRTLSSPLYRRIILGSGPNNQELFV-L DGTEFSFASLTTNLPST
CRYAA3 SLTGLGIFRTLSSPLYRRIILGSGPNNQELFV L DGTEFSFASLTTNLPST

CRYAA1 IYRQRGTVDSLDVIPPQDNSVPPRAGFSHRLSH VTMLSQAAGAVYTLRAP
CRYAA4 IYRQRGTVDSLDVIPPQDNSVPPRAGFSHRLSH VTMLSQAAGAVYTLRAP
CRYAA5 IYRQRGTVDSLDVIPPQDNSVPPRAGFSHRLSH-VTMLSQAAGAVYTLRAP
CRYAA6 IYRQRGTVDSLDVIPPQDNSVPPRAGFSHRLSH VTMLSQAAGAVYTLRAP
CRYAA2 IYRQRGTVDSLDVIPPQDNSVPPRAGFSHRLSH-VTMLSQAAGAVYTLRAP
CRYAA3 IYRQRGTVDSLDVIPPQDNSVPPRAGFSHRLSH VTMLSQAAGAVYTLRAP

FIG. 7C

| | | |
|---|---|---|
| CRYAA1 | TFSWQHRSAEFNNIIPSSQITQIPL TKSTNLGS GTSVVKGPGFTGGDILR | |
| CRYAA4 | TFSWQHRSAEFNNIIPSSQITQIPL TKSTNLGS-GTSVVKGPGFTGGDILR | |
| CRYAA5 | TFSWQHRSAEFNNIIPSSQITQIPL TKSTNLGS GTSVVKGPGFTGGDILR | |
| CRYAA6 | TFSWQHRSAEFNNIIPSSQITQIPL TKSTNLGS GTSVVKGPGFTGGDILR | |
| CRYAA2 | TFSWQHRSAEFNNIIPSSQITQIPL TKSTNLGS-GTSVVKGPGFTGGDILR | |
| CRYAA3 | TFSWQHRSAEFNNIIPSSQITQIPL TKSTNLGS GTSVVKGPGFTGGDILR | |

| | | |
|---|---|---|
| CRYAA1 | RTSPGQISTLRVNITAPLSQRYRVRIRYASTTN LQFHTSIDGRPINQGNF | |
| CRYAA4 | RTSPGQISTLRVNITAPLSQRYRVRIRYASTTN-LQFHTSIDGRPINQGNF | |
| CRYAA5 | RTSPGQISTLRVNITAPLSQRYRVRIRYASTTN LQFHTSIDGRPINQGNF | |
| CRYAA6 | RTSPGQISTLRVNITAPLSQRYRVRIRYASTTN LQFHTSIDGRPINQGNF | |
| CRYAA2 | RTSPGQISTLRVNITAPLSQRYRVRIRYASTTN-LQFHTSIDGRPINQGNF | |
| CRYAA3 | RTSPGQISTLRVNITAPLSQRYRVRIRYASTTN LQFHTSIDGRPINQGNF | |

| | | |
|---|---|---|
| CRYAA1 | SATMSSGSNLQSGSFRTVGFTTPFNFSNGSSVF TLSAHVFNSGNEVYIDR | |
| CRYAA4 | SATMSSGSNLQSGSFRTVGFTTPFNFSNGSSVF-TLSAHVFNSGNEVYIDR | |
| CRYAA5 | SATMSSGSNLQSGSFRTVGFTTPFNFSNGSSVF TLSAHVFNSGNEVYIDR | |
| CRYAA6 | SATMSSGSNLQSGSFRTVGFTTPFNFSNGSSVF TLSAHVFNSGNEVYIDR | |
| CRYAA2 | SATMSSGSNLQSGSFRTVGFTTPFNFSNGSSVF-TLSAHVFNSGNEVYIDR | |
| CRYAA3 | SATMSSGSNLQSGSFRTVGFTTPFNFSNGSSVF TLSAHVFNSGNEVYIDR | |

| | | |
|---|---|---|
| CRYAA1 | IEFVPAEVT | 609 |
| CRYAA4 | IEFVPAEVT | 609 |
| CRYAA5 | IEFVPAEVT | 609 |
| CRYAA6 | IEFVPAEVT | 609 |
| CRYAA2 | IEFVPAEVT | 609 |
| CRYAA3 | IEFVPAEVT | 609 |

FIG. 7D

SEQUENCE LISTING

<160> NUMBER OF SEQ ID NOS: 10

<210> SEQ ID NO 1
<211> LENGTH: 641
<212> TYPE: PRT
<213> ORGANISM: Bacillus thuringiensis

<400> SEQUENCE: 1

Met Ala Ile Val Asn Asn Gln Asn Gln Cys Val Pro Tyr Asn Cys Leu
1               5                   10                  15

Asn Asn Pro Glu Asn Glu Ile Leu Asp Ile Glu Arg Ser Asn Ser Thr
            20                  25                  30

Val Ala Thr Asn Ile Ala Leu Glu Ile Ser Arg Leu Leu Ala Ser Ala
        35                  40                  45

Thr Pro Ile Gly Gly Ile Leu Leu Gly Leu Phe Asp Ala Ile Trp Gly
    50                  55                  60

Ser Ile Gly Pro Ser Gln Trp Asp Leu Phe Leu Glu Gln Ile Glu Leu
65                  70                  75                  80

Leu Ile Asp Gln Lys Ile Glu Glu Phe Ala Arg Asn Gln Ala Ile Ser
                85                  90                  95

-continued

```
Arg Leu Glu Gly Ile Ser Ser Leu Tyr Gly Ile Tyr Thr Glu Ala Phe
            100                 105                 110
Arg Glu Trp Glu Ala Asp Pro Thr Asn Pro Ala Leu Lys Glu Glu Met
        115                 120                 125
Arg Thr Gln Phe Asn Asp Met Asn Ser Ile Leu Val Thr Ala Ile Pro
    130                 135                 140
Leu Phe Ser Val Gln Asn Tyr Gln Val Pro Phe Leu Ser Val Tyr Val
145                 150                 155                 160
Gln Ala Ala Asn Leu His Leu Ser Val Leu Arg Asp Val Ser Val Phe
                165                 170                 175
Gly Gln Ala Trp Gly Phe Asp Ile Ala Thr Ile Asn Ser Arg Tyr Asn
            180                 185                 190
Asp Leu Thr Arg Leu Ile Pro Ile Tyr Thr Asp Tyr Ala Val Arg Trp
        195                 200                 205
Tyr Asn Thr Gly Leu Asp Arg Leu Pro Arg Thr Gly Gly Leu Arg Asn
    210                 215                 220
Trp Ala Arg Phe Asn Gln Phe Arg Arg Glu Leu Thr Ile Ser Val Leu
225                 230                 235                 240
Asp Ile Ile Ser Phe Phe Arg Asn Tyr Asp Ser Arg Leu Tyr Pro Ile
                245                 250                 255
Pro Thr Ser Ser Gln Leu Thr Arg Glu Val Tyr Thr Asp Pro Val Ile
            260                 265                 270
Asn Ile Thr Asp Tyr Arg Val Gly Pro Ser Phe Glu Asn Ile Glu Asn
        275                 280                 285
Ser Ala Ile Arg Ser Pro His Leu Met Asp Phe Leu Asn Asn Leu Thr
    290                 295                 300
Ile Asp Thr Asp Leu Ile Arg Gly Val His Tyr Trp Ala Gly His Arg
305                 310                 315                 320
Val Thr Ser His Phe Thr Gly Ser Ser Gln Val Ile Thr Thr Pro Gln
                325                 330                 335
Tyr Gly Ile Thr Ala Asn Ala Glu Pro Arg Arg Thr Ile Ala Pro Ser
            340                 345                 350
Thr Phe Pro Gly Leu Asn Leu Phe Tyr Arg Thr Leu Ser Asn Pro Phe
        355                 360                 365
Phe Arg Arg Ser Glu Asn Ile Thr Pro Thr Leu Gly Ile Asn Val Val
    370                 375                 380
Gln Gly Val Gly Phe Ile Gln Pro Asn Asn Ala Glu Val Leu Tyr Arg
385                 390                 395                 400
Ser Arg Gly Thr Val Asp Ser Leu Asn Glu Leu Pro Ile Asp Gly Glu
                405                 410                 415
Asn Ser Leu Val Gly Tyr Ser His Arg Leu Ser His Val Thr Leu Thr
            420                 425                 430
Arg Ser Leu Tyr Asn Thr Asn Ile Thr Ser Leu Pro Thr Phe Val Trp
        435                 440                 445
Thr His His Ser Ala Thr Asn Thr Asn Thr Ile Asn Pro Asp Ile Ile
    450                 455                 460
Thr Gln Ile Pro Leu Val Lys Gly Phe Arg Leu Gly Gly Gly Thr Ser
465                 470                 475                 480
Val Ile Lys Gly Pro Gly Phe Thr Gly Gly Asp Ile Leu Arg Arg Asn
                485                 490                 495
Thr Ile Gly Glu Phe Val Ser Leu Gln Val Asn Ile Asn Ser Pro Ile
            500                 505                 510
```

```
Thr Gln Arg Tyr Arg Leu Arg Phe Arg Tyr Ala Ser Ser Arg Asp Ala
            515                 520                 525
Arg Val Ile Val Leu Thr Gly Ala Ala Ser Thr Gly Val Gly Gly Gln
        530                 535                 540
Val Ser Val Asn Met Pro Leu Gln Lys Thr Met Glu Ile Gly Glu Asn
545                 550                 555                 560
Leu Thr Ser Arg Thr Phe Arg Tyr Thr Asp Phe Ser Asn Pro Phe Ser
                565                 570                 575
Phe Arg Ala Asn Pro Asp Ile Ile Gly Ile Ser Glu Gln Pro Leu Phe
            580                 585                 590
Gly Ala Gly Ser Ile Ser Ser Gly Glu Leu Tyr Ile Asp Lys Ile Glu
        595                 600                 605
Leu Ile Leu Ala Asp Ala Thr Phe Lys Arg Arg Arg Trp Ser Val His
    610                 615                 620
Lys Ala Ser Arg Pro Leu His Leu His Gln Gln Ala Gly Leu Ala Ala
625                 630                 635                 640
Asp

<210> SEQ ID NO 2
<211> LENGTH: 1990
<212> TYPE: DNA
<213> ORGANISM: Bacillus thuringiensis

<400> SEQUENCE: 2
cccgcatgcc ccggggatc caagctttaa accatggcta tcgttaacaa ccagaaccag       60
tgcgtccctt acaattgcct caacaaccca gagaacgaga tcttggacat cgaaagatcc     120
aattctaccg tggccaccaa cattgctctt gagatttcca gattgctcgc tagcgcaact    180
cccattggtg gcatcctcct tggattgttc gacgccattt ggggttccat cggaccatca    240
caatgggatc tcttccttga acagatcgag ttgctcattg accagaagat cgaagagttt    300
gctaggaacc aggcaattag ccgtctcgag gggatctctt ccctttacgg aatctataca    360
gaggccttca gagagtggga agctgaccct actaatccag cattgaagga agagatgcgt    420
actcaattca acgatatgaa ctctatcttg gtcaccgcca ttcctctctt ctcagtgcag    480
aactaccaag tgccattcct ctccgtctat gttcaagctg caaacttgca cctttctgtc    540
cttcgcgacg tgtccgtctt tggtcaagcc tggggcttcg atatcgctac tatcaactcc    600
cgttacaacg acctcacaag gttgattcct atctacactg actacgctgt tagatggtac    660
aatactgggc ttgacagact cccacgtacc ggcggattga ggaattgggc tcgcttcaac    720
cagtttaggc gtgagctcac cattagcgtg ttggacatca tttccttctt cagaaactac    780
gactctagac tttatcctat tccaactagt tctcaactca ccagggaggt ctacaccgat    840
cctgtgatca acattaccga ctatcgtgtg ggtccctcct tcgagaacat gaaaacagc    900
gctatcagat ctccacacct tatggacttc tcaataact tgactatcga tacagacctt     960
atcagaggtg ttcactactg ggctggccat agggtcacct ctcactttac cggtagttcc   1020
caagtgatca caacccctca atacggaatt actgccaacg cagagccaag acgtaccatt   1080
gctccaagta cctttcccgg gttgaacctc ttctaccgca cattgtcaaa tccattcttc   1140
aggagatctg agaacatcac ccctaccctt gggatcaacg ttgtccaggg agtgggtttc   1200
atccagccaa caatgctga ggtgctctac aggtctagag cacagtggga ctccttgaac   1260
gaacttccaa ttgacggtga gaactcactc gtcggataca gtcaccgtct tagccacgtt    1320
actttgacca ggtctctcta taacactaat atcactagtt tgcccacctt cgtgtggact    1380
```

-continued

```
caccactcag ccaccaacac aaacactatc aatcccgata tcattacaca aatccccctt   1440
gtcaagggct tccgcttggg tggagggacc tccgtcatta aagggcccgg attcaccggt   1500
ggcgatatcc tccgtagaaa caccattggt gagtttgtgt ccctccaggt taacattaac   1560
tctcctatca cacaaaggta ccgtcttagg ttccgctacg cttcctctag agacgcaaga   1620
gtcattgtgc ttaccggtgc cgcttccaca ggagtcggtg ccaagtcag cgttaacatg    1680 ccattgcaaa agactatgga gatcggagag aacctcacta gtagaacctt caggtatacc   1740
gacttctcta accctttctc cttccgtgct aacccagata tcattggcat cagcgaacaa   1800
cctctcttcg gcgccggctc catcagctct ggtgaactct acatcgataa gatcgagttg   1860
atccttgctg acgccacatt caagaggaga cgatggagcg tgcacaaagc ctcacgccct   1920
cttcacctcc accaacaagc tggactcgct gctgattaat gagaattcgg atccaagctt   1980
gggcccgctc                                                          1990
```

<210> SEQ ID NO 3
<211> LENGTH: 609
<212> TYPE: PRT
<213> ORGANISM: Bacillus thuringiensis

<400> SEQUENCE: 3

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
             20                  25                  30

Tyr Thr Pro Ile Asp Ile Ser Leu Ser Leu Thr Gln Phe Leu Leu Ser
         35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Pro Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255
```

```
Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Val Leu Val Ser Leu
            340                 345                 350

Thr Gly Leu Gly Ile Phe Arg Thr Leu Ser Ser Pro Leu Tyr Arg Arg
            355                 360                 365

Ile Ile Leu Gly Ser Gly Pro Asn Asn Gln Glu Leu Phe Val Leu Asp
370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
            405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
            435                 440                 445

Ala Pro Thr Phe Ser Trp Gln His Arg Ser Ala Glu Phe Asn Asn Ile
        450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
            595                 600                 605

Thr

<210> SEQ ID NO 4
<211> LENGTH: 609
<212> TYPE: PRT
<213> ORGANISM: Bacillus thuringiensis
```

```
<400> SEQUENCE: 4

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Pro Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415
```

```
Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
            435                 440                 445

Ala Pro Thr Phe Ser Trp Gln His Arg Ser Ala Glu Phe Asn Asn Ile
            450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
            515                 520                 525

Ala Ser Thr Thr Asn Leu Gln Phe His Thr Ser Ile Asp Gly Arg Pro
            530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
            595                 600                 605

Thr

<210> SEQ ID NO 5
<211> LENGTH: 609
<212> TYPE: PRT
<213> ORGANISM: Bacillus thuringiensis

<400> SEQUENCE: 5

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
            85                  90                  95

Ile Ser Arg Leu Glu Gly Leu Ser Asn Leu Tyr Gln Ile Tyr Ala Glu
        100                 105                 110

Ser Phe Arg Glu Trp Glu Ala Asp Pro Thr Asn Pro Ala Leu Arg Glu
    115                 120                 125

Glu Met Arg Ile Gln Phe Asn Asp Met Asn Ser Ala Leu Thr Thr Ala
130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
            165                 170                 175
```

```
Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590
```

Gly Asn Glu Val Tyr Ile Asp Arg Ile Glu Phe Val Pro Ala Glu Val
            595                 600                 605
Thr

<210> SEQ ID NO 6
<211> LENGTH: 609
<212> TYPE: PRT
<213> ORGANISM: Bacillus thuringiensis

<400> SEQUENCE: 6

Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Leu Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
            405                 410                 415

Gln Asp Asn Ser Val Pro Pro Arg Ala Gly Phe Ser His Arg Leu Ser
                420                 425                 430

His Val Thr Met Leu Ser Gln Ala Ala Gly Ala Val Tyr Thr Leu Arg
            435                 440                 445

Ala Pro Thr Phe Ser Trp Gln His Arg Ser Ala Glu Phe Asn Asn Ile
        450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr

<210> SEQ ID NO 7
<211> LENGTH: 609
<212> TYPE: PRT
<213> ORGANISM: Bacillus thuringiensis

<400> SEQUENCE: 7

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

-continued

```
Ser Phe Arg Glu Trp Glu Ala Asp Pro Thr Asn Pro Ala Leu Arg Glu
    115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285

Gln Asn Ile Arg Gln Pro His Leu Met Asp Ile Leu Asn Arg Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
    370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
    450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525
```

```
Ala Ser Thr Thr Asn Leu Gln Phe His Thr Ser Ile Asp Gly Arg Pro
    530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
                580                 585                 590

Gly Asn Glu Val Tyr Ile Asp Arg Ile Glu Phe Val Pro Ala Glu Val
            595                 600                 605

Thr

<210> SEQ ID NO 8
<211> LENGTH: 609
<212> TYPE: PRT
<213> ORGANISM: Bacillus thuringiensis

<400> SEQUENCE: 8

Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
                 20                  25                  30

Tyr Thr Pro Ile Asp Ile Ser Leu Ser Leu Thr Gln Phe Leu Leu Ser
             35                  40                  45

Glu Phe Val Pro Gly Ala Gly Phe Val Leu Gly Leu Val Asp Ile Ile
     50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
        275                 280                 285
```

```
Gln Asn Ile Arg Gln Pro His Leu Met Asp Ile Leu Asn Ser Ile Thr
    290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Val Leu Val Ser Leu
            340                 345                 350

Thr Gly Leu Gly Ile Phe Arg Thr Leu Ser Ser Pro Leu Tyr Arg Arg
        355                 360                 365

Ile Ile Leu Gly Ser Gly Pro Asn Asn Gln Glu Leu Phe Val Leu Asp
370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
        435                 440                 445

Ala Pro Thr Phe Ser Trp Gln His Arg Ser Ala Glu Phe Asn Asn Ile
450                 455                 460

Ile Pro Ser Ser Gln Ile Thr Gln Ile Pro Leu Thr Lys Ser Thr Asn
465                 470                 475                 480

Leu Gly Ser Gly Thr Ser Val Val Lys Gly Pro Gly Phe Thr Gly Gly
                485                 490                 495

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
        515                 520                 525

Ala Ser Thr Thr Asn Leu Gln Phe His Thr Ser Ile Asp Gly Arg Pro
530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
        595                 600                 605

Thr

<210> SEQ ID NO 9
<211> LENGTH: 12
<212> TYPE: DNA
<213> ORGANISM: Artificial Sequence
<220> FEATURE:
<223> OTHER INFORMATION: Synthetically generated oligonucleotide

<400> SEQUENCE: 9
taaaccatgg ct                                                         12

<210> SEQ ID NO 10
<211> LENGTH: 1990
<212> TYPE: DNA
<213> ORGANISM: Bacillus thuringiensis
```

```
<400> SEQUENCE: 10
gagcgggccc aagcttggat ccgaattctc attaatcagc agcgagtcca gcttgttggt    60
ggaggtgaag agggcgtgag gctttgtgca cgctccatcg tctcctcttg aatgtggcgt   120
cagcaaggat caactcgatc ttatcgatgt agagttcacc agagctgatg gagccggcgc   180
cgaagagagg ttgttcgctg atgccaatga tatctgggtt agcacggaag gagaaagggt   240
tagagaagtc ggtatacctg aaggttctac tagtgaggtt ctctccgatc tccatagtct   300
tttgcaatgg catgttaacg ctgacttggc caccgactcc tgtggaagcg caccggtaa    360 gcacaatgac tcttgcgtct ctagaggaag cgtagcggaa cctaagacgg taccttttgtg  420 tgataggaga gttaatgtta acctggaggg acacaaactc accaatggtg tttctacgga   480
ggatatcgcc accggtgaat ccgggccctt taatgacgga ggtccctcca cccaagcgga   540
agcccttgac aagggggatt tgtgtaatga tatcgggatt gatagtgttt gtgttggtgg   600
ctgagtggtg agtccacacg aaggtgggca aactagtgat attagtgtta tagagagacc   660
tggtcaaagt aacgtggcta agacggtgac tgtatccgac gagtgagttc tcaccgtcaa   720
ttggaagttc gttcaaggag tccactgtgc ctctagacct gtagagcacc tcagcattgt   780
ttggctggat gaaacccact ccctggacaa cgttgatccc aagggtaggg gtgatgttct   840
cagatctcct gaagaatgga tttgacaatg tgcggtagaa gaggttcaac ccgggaaagg   900
tacttggagc aatggtacgt cttggctctg cgttggcagt aattccgtat tgaggggttg   960
tgatcacttg ggaactaccg gtaaagtgag aggtgaccct atggccagcc cagtagtgaa  1020
cacctctgat aaggtctgta tcgatagtca agttattgag gaagtccata aggtgtggag  1080
atctgatagc gctgtttttca atgttctcga aggagggacc cacacgatag tcggtaatgt  1140
tgatcacagg atcggtgtag acctccctgg tgagttgaga actagttgga ataggataaa  1200
gtctagagtc gtagttttctg aagaaggaaa tgatgtccaa cacgctaatg gtgagctcac  1260
gcctaaactg gttgaagcga gcccaattcc tcaatccgcc ggtacgtggg agtctgtcaa  1320
gcccagtatt gtaccatcta acagcgtagt cagtgtagat aggaatcaac cttgtgaggt  1380
cgttgtaacg ggagttgata gtagcgatat cgaagcccca ggcttgacca aagacggaca  1440
cgtcgcgaag gacagaaagg tgcaagtttg cagcttgaac atagacggag aggaatggca  1500
cttggtagtt ctgcactgag aagagaggaa tggcggtgac caagatagag ttcatatcgt  1560
tgaattgagt acgcatctct tccttcaatg ctggattagt agggtcagct tcccactctc  1620
tgaaggcctc tgtatagatt ccgtaaaggg aagagatccc ctcgagacgg ctaattgcct  1680
ggttcctagc aaactcttcg atcttctggt caatgagcaa ctcgatctgt tcaaggaaga  1740
gatcccattg tgatggtccg atggaacccc aaatggcgtc gaacaatcca aggaggatgc  1800
caccaatggg agttgcgcta gcgagcaatc tggaaatctc aagagcaatg ttggtggcca  1860
cggtagaatt ggatctttcg atgtccaaga tctcgttctc tgggttgttg aggcaattgt  1920
aagggacgca ctggttctgg ttgttaacga tagccatggt ttaaagcttg atcccccgg   1980 ggcatgcggg                                                         1990
```

CHIMERIC CRYLE δ ENDOTOXIN AND METHODS OF CONTROLLING INSECTS

CLAIM OF PRIORITY

This application is a divisional (and claims the benefit of priority under 35 U.S.C. § 120) of U.S. application Ser. No. 10/107,581, filed Mar. 27, 2002 now U.S. Pat. No. 7,053,266. The disclosure of the prior application is considered part of (and is incorporated by reference in) the disclosure of this application.

FIELD OF THE PRESENT INVENTION

The present invention relates to a chimeric δ endotoxin protein Cry 1E of SEQ ID No. 1 with extraordinarily high insecticidal property and a chimera gene of SEQ ID No. 2 (antisense sequence is depicted in SEQ ID No. 10) encoding the said chimeric protein, and also a method of treating insect infested plants using said chimera protein.

BACKGROUND OF THE INVENTION

Damage due to insects costs billions of dollars annually in form of crop losses and in the expense of keeping these pests under control. The losses caused by pests in agricultural production environments include decrease in crop yield, poor crop quality, increased harvesting costs, and loss to health and environment.

Reference may be made to Hofte H. and Whiteley H. R., 1989, "Insecticidal crystal protein of *Bacillus thuringiensis*", Microbiol. Rev. 53: 242-255, wherein *Bacillus thuringiensis* (B.t.) is a ubiquitous gram-positive spore-forming soil bacterium, known for its ability to produce parasporal crystalline inclusions during sporulation. These inclusions consist of proteins known as crystal proteins or Cry proteins or δ-endotoxins, which exhibit insecticidal activity, particularly against larvae of insect species in orders lepidoptera, diptera and coleoptera. Proteins with toxicity to insects of orders hymenoptera, homoptera, orthoptera, mallophaga; nematodes; mites and protozoans have also been mentioned in literature (Feitelson J. S., 1993, "The *Bacillus thuringiensis* family tree", 63-71, In L. kim ed. Advanced engineered pesticides. Marcel Dekker. Inc., New York., N.Y. and Feitelson et al., 1992, "*Bacillus thuringiensis*: insects and beyond", Bio/Tech. 10: 271-275; may be sited for this). Several strains of *Bacillus thuringiensis* (B.t.) have been identified with different host spectra and classified into different subspecies or serotypes on the basis of flagellar antigens. Pasteur Institute, France has catalogued 55 different flagellar serotypes and 8 non-flagellated biotypes. The reference may be made to Schnepf et al., 1998, "*Bacillus thuringiensis* and its pesticidal crystal proteins", Microbiol. Mol. Biol. Riv. 62: 775-806, wherein several B.t. toxin-coding genes have been cloned, sequenced, characterized and recombinant DNA-based products have been produced and approved for commercial use. Through the employment of genetic engineering techniques, new approaches have been developed for delivering these B.t. toxins to agricultural environments, including the use of the genetically engineered crops and the stabilised intact microbial cells as δ-endotoxin delivery vehicles (Gaertner, F. H., Kim L., 1988, TIBTECH 6: 54-57). Thus, δ-endotoxin genes coding for proteins targeted to kill hosts, especially pests and insects that cause economic losses are becoming commercially valuable.

Commercial use of B.t. pesticides in a given crop environment is limited because a given δ-endotoxin shows toxicity to a narrow range of target pests. Preparations of the spores and crystals of *B. thuringiensis* subsp. *kurstaki* have been used for many years as commercial insecticides against lepidopteran pests. For example, *B. thuringiensis* var. *kurstaki* HD-1 produces several δ-endotoxins, and is therefore toxic to a relatively broader range of lepidopteran insects. However, formulations based on the known δ-endotoxins, including B.t.k. HD-1 are not effective against some of the important crop pests, like *Spodoptera* sp. that also belong to order lepidoptera. Other species of B.t., namely *israelensis* and *tenebrionis* have been used commercially to control certain insects of the orders diptera and coleoptera, respectively (Gaertner, F. H., 1989, "Cellular Delivery Systems for Insecticidal Proteins: Living and Non-Living Microorganisms," in Controlled Delivery of Crop Protection Agents, R. M. Wilkins, ed., Taylor and Francis, New York and London, 1990, pp. 245-255; Couch T. L., 1980, "Mosquito Pathogenicity of *Bacillus thuringiensis* var. *israelensis*", Development in Industrial Microbiology 22: 61-76 and Beegle C. C., 1978, "Use of Entomogenous Bacteria in Agroecosystems", "Developments in Industrial Microbiology 20: 97-104; may be sited for this). Kreig et. al. (1983) in Z. ang. Ent. 96: 500-508, describe *Bacillus thuringiensis* var. *tenebrionis*, which is reportedly active against two beetles in the order Coleoptera i.e., Colorado potato beetles, *Leptinotarsa decemlineata* and *Agelastica alni*.

Reference may be made to Crickmore et. al., 1998, "Revision in the nomenclature for the *Bacillus thuringiensis* pesticidal crystal proteins", Microbiol. Mol. Biol. Rev. 62: 807-813, wherein crystal protein genes are classified into 22 classes, primarily on the basis of amino acid sequence homology. The cloning and expression of a B.t. crystal protein gene in *Escherichia coli* has been described in several cases in the published literature (Schnepf et al., 1981, "Cloning and expression of the *Bacillus thuringiensis* crystal protein gene in *Escherichia coli*" may be cited for this). U.S. Pat. Nos. 4,448,885 and 4,467,036 disclose the expression of B.t. crystal protein in *E. coli*. U.S. Pat. Nos. 4,797,276 and 4,853,331 disclose *B. thuringiensis* strain *tenebrionis*, which can be used to control coleopteran pests in various environments. U.S. Pat. No. 4,918,006 discloses B.t. toxins having activity against dipterans. U.S. Pat. No. 4,849,217 discloses B.t. isolates, which have activity against the alfalfa weevil. U.S. Pat. No. 5,208,017 discloses coelopteran-active *Bacillus thuringiensis* isolates. U.S. Pat. Nos. 5,151,363 and 4,948,734 disclose certain isolates of B.t., which have activity against nematodes. Extensive research and resources are being spent to discover new B.t. isolates and their uses. As of now, the discovery of new B.t. isolates and new uses of the known B.t. isolates remains an empirical, unpredictable art. Several laboratories all over the world are trying to isolate new δ-endotoxin genes from *B. thuringiensis* for different host range and mechanism of action.

Bulla et al., 1980, "Ultrastructure, physiology and biochemistry of *Bacillus thuringiensis*". CRC Crit. Rev. Microbiol. 8: 147-204 and Grochulski et al., 1995, "*Bacillus thuringiensis* CryIA(a) insecticidal toxin: crystal structure and channel formation", J. Mol. Biol, 254: 447-464; have reported that majority of B.t. insecticidal crystal proteins are synthesised in natural form as protoxins (molecular weight 130-140 kDa), which form parasporal inclusions by virtue of hydrophobic interactions, hydrogen bondings and disulfide bridges. The protoxins, which are not toxic to insect larvae, are composed of two segments the—N-terminal half and C-terminal half. The protoxins are converted into functionally active toxins (60-70 kDa) in insect mid gut following their site-specific cleavage by proteases at alkaline pH. Such proteolytically processed, truncated δ-endotoxins bind to specific receptors in insect mid-gut and cause mortality by making pores in the epithelial membrane (the references, Bietlot et al., 1989, "Facile preparation and characterization of the toxin from *Bacillus thuringensis* var. *kurstaki*", Biochem. J., 260: 87-91; Choma et al., 1990, "Unusual proteolysis of the protoxin and toxin from *Bacillus thuringensis*: structural implications", Eur. J. Biochem. 189: 523-27; and Hofte et al., 1986, "Structural and functional analysis of a cloned delta endotoxin of *Bacillus thuringensis berliner* 1715", Eur. J. Biochem. 161: 273-280; may be cited for this). The protease-resistant active toxin corresponds to N-terminal half of the protoxin molecule. The other segment corresponding to C-terminal half is believed to be required for the formation of highly stable crystals. During the proteolytic processing, a small polypeptide comprising about 25-30 amino acid residues is removed from N-terminal of the protoxin.

The crystal structure of the core toxic segment of Cry1Aa and Cry3Aa δ-endotoxins are known (Grochulsky et al., 1995, "*Bacillus thuringensis* CryIA(a) insecticidal toxin: crystal structure and channel formation", J. Mol. Biol. 254: 447-464 and Li et al., 1991, "Crystal structure of insecticidal δ-endotoxin from *Bacillus thuringiensis* at 2.5 Å resolution", Nature. 353: 815-821) and their three-dimensional structures are superimposable. Reasonably conserved polypeptide domains suggest that related toxins have similar topological structure. These are globular molecules composed of 3 distinct structural domains connected by small peptide linkers. There are no crossovers of the polypeptide chains between the domains. Domain I consists of 7 α helical structures. Domain II consists of three anti-parallel β-sheets and two short α-helices. Domain III is a β-sandwich of two anti-parallel highly twisted β-sheets. Domains II and III are located on the side where they face helix α 7 of domain I. These domains are closely packed by virtue of numerous van der Wall forces, hydrogen bonds and electrostatic interactions (salt bridges) between the domains.

One of the major reasons for narrow host range of δ-endotoxins is that these proteins need specific receptors in the insect gut in order to make pores and cause toxicity. Since a given δ-endotoxin exhibits toxicity to a very narrow range of insects, it is desirable to engineer these proteins for modifying their receptor recognition in larval midgut, to widen host range and to improve toxicity. Two approaches have been followed for this purpose—first, the development of chimeric (or hybrid) genes by exchanging functional domains of the proteins and secondly, the development of improved δ-endotoxin proteins by site directed mutagenesis. References may be made to U.S. Pat. Nos. 5,128,130 and 5,055,294 wherein hybrid B.t. crystal proteins have been constructed, which exhibit increased toxicity and display an expanded host range to the target pests.

The reference may be made to Honee et al., 1990, "A translation fusion product of two different insecticidal crystal protein gene of *Bacillus thuringensis* exhibits an enlarged insecticidal spectrum" Appl. Environ. Microbiol. 56: 823-825, wherein translational fusion of two cry genes (cry1Ab and cry1Ca) has been made. The resulting hybrid protein had wider toxicity spectrum that overlapped those of the two contributing parental crystal proteins. However, the drawback is that the activity of the chimeric toxin did not increased over any of the parental toxins towards the target insect pests. In spite of poor toxicity, fusion gene was expressed in tobacco after partial modification, which conferred only partial protection to transgenic plants against a broader range of insects, including *Spodoptera exigua, Heliothis virescens* and *Manduca sexta* (the reference, van der Salm et al., 1994, "Insect resistance of transgenic plants that express modified *Bacillus thuringensis* cryIAb and cryIC genes: a resistance management strategy", Plant Mol. Biol. 26: 51-59, may be cited for this).

The reference may be made to Honee et al., 1991, "The C-terminal domain of the toxic fragment of *Bacillus thuringensis* crystal protein determines receptor binding", Mol. Microbiol. 5: 2799-2806, wherein 11 chimeric genes have been constructed using cry1Ab and cry1Ca as parent genes by exchanging functional domains. The draw back is that only two chimeric proteins, in which pore-forming domains had been exchanged, exhibited insecticidal activity. However, the efficacy of the toxin chimeric proteins was lower than the parental proteins. Other hybrid proteins were non-toxic.

Masson et al., 1992, "Insecticidal properties of a crystal protein gene product isolated from *Bacillus thuringensis* subsp. *kenyae*", Appl. Environ. Microbiol. 58: 2, 642-646, reported that one of the Cry1 δ-endotoxins, namely Cry1Ea does not exhibit toxicity against *Spodoptera* larvae. Further, the reference may be made to Bosch et al., 1994, "Recombinant *Bacillus thuringensis* Crystal protein with new properties: possibilities for resistance management", Bio/Tech 12: 915-918, wherein many chimeric genes have been developed following in vivo recombination of cry1Ca and cry1Ea genes. The δ-endotoxin expressed from one of the chimeric genes, which consisted of domain I and II of Cry1Ea and domain III of Cry1Ca protein exhibited larvicidal activity. The transfer of domain III of Cry1Ca to Cry1Ea protein gave an insecticidal protein. However, the chimeric toxin was not an improved toxin over the Cry1Ca, which is best-reported toxin to *Spodoptera* sp. Another chimeric toxin exhibited very poor toxicity. The remaining chimeric toxins were either unstable or non-toxic.

Reference may be cited as Rang et al., 1999, "Interaction between functional domain of *Bacillus thuringensis* insecticidal crystal protein", Appl Environ Microbiol, 65, 7: 2918-25, wherein many chimeric genes have been developed by exchanging the regions coding for either domain I or domain III among Cry1Ab, Cry1Ac, Cry1Ca and Cry1Ea δ-endotoxins and checked their stability in *E. coli* and plasma membrane permeability of Sf9 cells. A chimeric toxin (consisting of domains I and II of Cry1Ca and domain III of Cry1Ab) was more toxic than the parental toxins. Exchange of domain III of Cry1Ab with that of Cry1Ca made the chimeric protein more active than the Cry1Ca protein. Proteins with the exchange of other domains were either unstable or less toxic than the parent proteins. However, the toxicity of the chimeric protein to insect larvae was not tested. Pore formation in insect cell line was compared but that cannot be correlated with the insecticidal activity of the δ-endotoxin.

Reference may be made to Chandra et al., 1999, "Amino acid substitution in alpha-helix 7 of Cry1Ac δ-endotoxin of *Bacillus thuringensis* leads to enhanced toxicity to *Helicoverpa armigera* Hubner", FEBS Lett. 458: 175-179; wherein a hydrophobic motif in the C-terminal end of the fragment B of diphtheria toxin was found to be homologous to helix α7 of δ-endotoxins. Upon substitution of helix α7 of Cry1Ac protein by this polypeptide, the chimeric protein exhibited 7-8 fold enhancement in toxicity towards *Helicoverpa armigera*. The increased toxicity was due to higher pore forming ability.

These examples establish the potential of protein engineering for the improvement of native toxins, to develop commercially useful δ-endotoxins.

Most of the lepidopteran pests are polyphagous in nature. *Spodoptera* is a common lepidopteran insect and its 5 species (*litura, littoralis, exigua, frugiperda* and *exempta*) are found worldwide. *Spodoptera littoralis* (the Egyptian cotton leaf worm, CLW) is a major pest of cotton and other crops of agronomical importance in Europe (the reference Mazier et al., 1997, "The cryIC gene from *Bacillus thuringensis* provides protection against *Spodoptera littoralis* in young transgenic plants", Plant Sci. 127: 179-190, may be cited for this). It is a notorious pest of cotton, groundnut, chilli, pulses and several vegetable crops, especially in warm and humid regions, as the southern parts of India. High fecundity, short life cycle, destructive feeding habits and often-reported emergence of resistance to chemical insecticides have made the control of *Spodoptera* an increasing agricultural problem. Reference may be made to Bai et al., 1993, "Activity of insecticidal proteins and strains of *Bacillus thuringensis* against *Spodoptera exempta* (Walker)" J. Inverteb. Pathol. 62: 211-215, wherein it is discussed that the young larvae are susceptible to certain δ-endotoxins, but the larvae beyond $2^{nd}$ instar display considerable tolerance. This has been attributed to the high content of alkaline proteases in the gut juice (the reference Keller et al., 1996, "Digestion of δ-endotoxin by gut proteases may explain reduced sensitivity of advanced instar larvae of *Spodoptera littoralis* to CryIC", Insect Biochem. Mol. Biol. 26: 365-373, may be cites for this).

Four different δ-endotoxins have been reported to cause low level of mortality to the *Spodoptera* sp. Of these, Cry1Ca is the most effective toxin. The plants expressing Cry1Ca at a high level caused mortality and hence conferred protection against early instar larvae (the references Mazier et al., 1997, "The cryIC gene from *Bacillus thuringiensis* provides protection against *Spodoptera littoralis* in young transgenic plants". Plant Sci. 127: 179-190 and Strizhov et al., 1996, "A synthetic cry1C gene, encoding a *Bacillus thuringensis* δ-endotoxin, confers *Spodoptera* resistance in alfalfa and tobacco" Proc. Natl. Acad. Sci. U.S.A. 93: 15012-15017 may be cited for this). However, complete protection against *Spodoptera* has not been reported in any case. The larvae in advanced developmental stages are not killed at moderate levels of the known δ-endotoxins. Hence, transgenic plants expressing Cry1Ca are not as effective as desirable in protection against *Spodoptera*. Other genes, like cry1Cb, cry1Ea and cry1F have not been employed for the development of transgenic plants against *Spodoptera* because of their comparatively low toxicity. Cry1Cb δ-endotoxin is 5-fold less toxic than Cry1Ca. The toxicity of Cry1Ea δ-endotoxin is very low and is disputed in certain reports (Masson et al., 1992 and Bosch et al., 1994 may be cited for this). Cry1F exhibits mild toxicity to *Spodoptera* larvae (Chambers et al., 1991 may be cited for this).

Reference may be made to Kalman et al., 1993, "Cloning of a novel cryIC-type gene from a strain of *Bacillus thuringensis* subsp. *Galleriae*", Appl. Environ. Microbiol. 59: 4: 1131-1137, wherein Cry1Cb δ-endotoxin is reported to be 5-fold less toxic than Cry1Ca. First two domains of these proteins are highly homologous (92% identical). A major difference is observed in domain III that exhibits only 48% homology. Higher toxicity (5-fold) of Cry1Ca over Cry1Cb δ-endotoxin suggested us that domain III of Cry1Ca might have an important role in its efficacy. The toxicity of Cry1Ea δ-endotoxin is very poor as it binds to the receptor very weakly in the midgut of *Spodoptera exigua* but the exchange of Domain III of Cry1Ca with Cry1Ea, made the latter toxic. This suggests the role of Domain III of Cry1C protein in receptor binding in the midgut of *Spodoptera* (the reference Bosch et. al., 1994, "Recombinant *Bacillus thuringensis* Crystal protein with new properties: possibilities for resistance management". Bio/Tech 12: 915-918, may be cited for this). In this publication, Bosch et al. (1994) established the advantage of hybrid toxin as it binds to a receptor where Cry1Ca does not bind. However, the toxicity of both, the native Cry1Ca and the hybrid Cry1Ea was comparable. They filed a patent (U.S. Pat. No. 5,736,131) in which 1.9-fold improvement in the toxicity towards *Spodoptera exigua* was claimed. The difference in results in the publication that reports no enhancement in toxicity and in the patent that claims 1.9 fold improved toxicity, makes the overall picture unclear.

Plant genetic engineering technology has made significant progress during the last 10 years. It has become possible to stably introduce foreign genes into plants. This has provided exciting opportunities for modern agriculture. Derivatives of the Ti-plasmid of the plant pathogen, *Agrobacterium tumefaciens*, have proven to be efficient and highly versatile vehicles for the introduction of foreign genes into plant tissue. In addition, a variety of methods to deliver DNA, such as electroporation, microinjection, pollen-mediated gene transfer and particle gun technology, have been developed for the same purpose.

The major aim of plant transformation by genetic engineering has been crop improvement. A substantial effort has been made for engineering the plants for useful traits such as insect-resistance. In this respect, progress in engineering insect resistance in transgenic plants has been achieved through the use of genes, encoding δ-endotoxins, from *B. thuringiensis* strains. Since δ-endotoxins possess a specific insecticidal spectrum and display no toxicity towards other non-host animals and humans, these are highly suited for developing commercially useful plants. No other protein is known which shows as high toxicity as (at ppm levels) and is still as safe to non-target organisms as the δ-endotoxins.

The feasibility of generating insect-resistant transgenic crops expressing δ-endotoxins and their success in commercial agriculture has been demonstrated. (References may be made to Vaeck et al., 1987, "Transgenic plants protected from insect attack", Nature. 328: 33-37; Fischoff et al., 1987, "Insect tolerant transgenic tomato plants", Bio/Tech. 5: 807-813"; Barton et al., 1987, "*Bacillus thuringensis* δ-endotoxin expressed in transgenic *Nicotiana tabaccum* provides resistance to lepidopteran insects", Plant Physiol. 85: 1103-1109 may be made for this). Transgenic plants offer an attractive alternative to insect control in agriculture, which is at the same time safe, environment friendly and cost-effective. Successful insect control has been observed under field conditions (Reference may be made to Delannay et al., 1989; Meeusen and Warren, 1989).

A reference may be cited to Von Tersch et al. 1991, "Insecticidal toxins from *Bacillus thuringensis* subsp *kanyae*: Gene cloning and characterization and comparison with *B. thuringiensis* subsp *kurstaki* Cry1A(c) toxin" in Appl and Environ Microbial, 57: 2: 349-58, wherein two variants of cry1Ac were isolated from two different strains. Their amino acid composition was different at 7 positions. Both the δ-endotoxins were expressed in *E. coli* and toxicity experiment was conducted. The two toxins did not exhibit any difference in efficacy towards target pests.

In another study (Schnepf et al., 1998, "*Bacillus thuringensis* and its pesticidal crystal proteins", 62: 3, 775-806), amino acid residues GYY of Cry1Ac δ-endotoxin at position 312 to 314 were altered to replace these with ASY, GSY and GFS. No difference in toxicity of the three proteins was noticed.

There are two natural variants of Cry1C δ-endotoxin namely Cry1Ca and Cry1Cb. These proteins show 81% (Schnepf et al., 1998, "*Bacillus thuringensis* and its pesticidal crystal proteins", 62: 3, 775-806) amino acid sequence identity. Despite this difference, both the toxins are toxic to their target pest, though there is some difference in the level of toxicity. Their host range is also same. (Kalman et al., 1993. "Cloning of a noval cry1C type gene from a strain of *Bacillus thuringensis* subsp *galleriae*" Appl. Environ Microbial 59: 4: 1131-37)

OBJECT OF THE PRESENT INVENTION

The main object of the present invention is to develop a chimeric δ endotoxin protein.

Another main object of the present invention is to develop a chimera gene coding for a chimeric δ endotoxin protein.

Yet another object of the present invention is to develop a method of developing said chimeric protein.

Still another object of the present invention is to develop a method of overexpressing said chimeric protein in a suitable microbe.

Still another object of the present invention is to develop a method of treating insect infested plants using said chimeric protein.

Further object of the present invention is to develop an insecticide for multidrug resistant insects.

Another object of the present invention is to develop an effective insecticide.

Yet another object of the present invention is to develop an insecticide having no adverse effect on the plants.

Still another object of the present invention is to develop an insecticide with about 100% insecticidal activity.

SUMMARY OF THE PRESENT INVENTION

The present invention relates to a chimeric δ endotoxin protein Cry 1E of SEQ ID No. 1 with extraordinarily high insecticidal property and a chimera gene of SEQ ID No. 2 encoding the said chimeric protein, and also a method of treating insect infested plants using said chimera protein.

DETAILED DESCRIPTION OF THE PRESENT INVENTION

Accordingly, the present invention relates to a chimeric δ endotoxin protein Cry 1E of SEQ ID No. 1 with extraordinarily high insecticidal property and a chimera gene of SEQ ID No. 2 encoding the said chimeric protein, and also a method of treating insect infested plants using said chimera protein.

In one embodiment of the present invention, a chimeric δ endotoxin protein Cry1E of SEQ ID No. 1 and other proteins of 75% and above homology in the sequence.

In another embodiment of the present invention, a chimeric δ endotoxin protein Cry1E of SEQ ID No. 1.

In yet another embodiment of the present invention, wherein said protein is of length 641 amino acid residues.

In still another embodiment of the present invention, wherein said chimeric protein is designed from δ endotoxins Cry1Ea and Cry1Ca of *Bacillus thuringensis*.

In still another embodiment of the present invention, wherein said chimeric protein of length of 641 residues is consisting of residues 1 to 529 from endotoxin Cry1Ea of same position, residues 530 to 599 from Cry1Ca of position 533 to 602, residues 600 to 616 from Cry1Ea of position 588 to 604 and residues 617 to 641 of a synthetic polypeptide.

In still another embodiment of the present invention, wherein peptide domain from 530 to 587 of Cry1Ea can be replaced with that of any other δ endotoxin.

In still another embodiment of the present invention, wherein last 25 amino acid residues improve the stability against the proteases of plants.

In still another embodiment of the present invention, wherein said chimeric protein is stable at temperature ranging between 4-35° C.

In further embodiment of the present invention, A chimera gene of SEQ ID No. 2.

In another embodiment of the present invention, wherein said chimera encodes chimeric protein of SEQ ID No. 1.

In still another embodiment of the present invention, wherein said chimera is of length 1990 base pairs (bp).

In still another embodiment of the present invention, wherein said chimera is a 1.99-kb double stranded DNA.

In still another embodiment of the present invention, wherein said chimera contains plant preferred codon distributed evenly to facilitate efficient translation.

In still another embodiment of the present invention, wherein said chimera contains plant preferred translation initiation codon of ATGGCT at 5' extreme.

In still another embodiment of the present invention, wherein said chimera contains plant preferred translation termination codon of TAATGA.

In still another embodiment of the present invention, wherein said chimera contains 33 restriction sites distributed uniformly throughout the length of the gene at a distance of about 40-80 bp.

In still another embodiment of the present invention, wherein restriction sites are enzymes selected from a group comprising Hind III, EcoRI, and BamHI.

In still another embodiment of the present invention, wherein said chimera is divided into 58 overlapping oligonucleotides of length 40 to 65 bp each located at a distance of 6 to 26 base pairs. (bp)

In still another embodiment of the present invention, wherein said chimera contains said overlapping nucleotides with an overlap of 13 to 18 nucleotides with the immediately adjacent oligonucleotides on the complementary strain.

In still another embodiment of the present invention, wherein said chimera has $T_m$ value ranging between 44 to 55° C.

In further embodiment of the present invention, a method of overexpressing insecticidal chimeric protein Cry1E in microbes.

In another embodiment of the present invention, cloning gene Cry1E of SEQ ID No. 2 encoding said chimeric protein in a vector.

In still another embodiment of the present invention, transforming microbe with said cloned vector.

In still another embodiment of the present invention, overexpressing said chimeric protein into said microbe.

In still another embodiment of the present invention, wherein said chimera is expressed into a microbe selected from a group comprising bacteria, algae, and fungi.

In still another embodiment of the present invention, wherein restriction enzymes for said cloning are selected from a group comprising Hind III, EcoRI, Ncol, Mfe I and BamHI.

In still another embodiment of the present invention, wherein inducing overexpression of said protein by using isopropylthiogalactoside (IPTG).

In still another embodiment of the present invention, wherein overexpressing said protein at 15° C. to avoid misfolding of said proteins.

In still another embodiment of the present invention, wherein said vectors are selected from a group comprising Plasmids, viral DNA, and cosmids.

In still another embodiment of the present invention, wherein expression of chimera in the microbe is confirmed by RT-PCR, western Analysis, and ELISA.

In still another embodiment of the present invention, wherein presence of chimera in the microbe is confirmed by PCR and southern Analysis.

In further embodiment of the present invention, a method of treating plants infected with insects using said insecticidal chimeric protein.

In another embodiment of the present invention, incorporating gene encoding chimera protein Cry1E into plant infected with insects.

In yet another embodiment of the present invention, exposing transgenic plant to insects.

In still another embodiment of the present invention, determining insecticidal activity of said transgenic plants.

In still another embodiment of the present invention, wherein insect pests are selected from a group comprising spodoptera sp., and Helicoverpa sp.

In still another embodiment of the present invention, wherein plants are selected from a group comprising tobacco, cotton, chickpea, pegeonpea, groundnut, cauliflower, cabbage, chilli, and capsicum.

In still another embodiment of the present invention, wherein restriction enzymes for said cloning are selected from a group comprising Hind III, EcoRI, Ncol, and BamHI.

In still another embodiment of the present invention, wherein chimeric protein shows high degree of expression in plants by having about 0.5% of total soluble protein of plants.

In still another embodiment of the present invention, wherein said chimeric protein is stable in said transgenic plant.

In still another embodiment of the present invention, wherein insects exposed to said chimeric protein show weight loss before death.

In still another embodiment of the present invention, wherein said chimeric protein shows insecticidal property against insect at all developmental stages.

In still another embodiment of the present invention, wherein said chimeric protein is multifold more potent insecticide as compared to parental proteins.

In still another embodiment of the present invention, wherein insecticidal activity of said chimeric protein shows mortality of insect pests ranging between 80-100% within about 4 hours of exposure.

In still another embodiment of the present invention, wherein insects exposed to said chimeric protein for about 1 hour shows delayed development, infertility and disrupted metamorphosis.

In still another embodiment of the present invention, wherein $EC_{50}$ for Helicoverpa sp. is ranging between 250-350 ng/ml of artificial diet of insects.

In still another embodiment of the present invention, wherein $EC_{50}$ of Spodoptera sp. is ranging between 25-50 ng/ml of artificial diet.

In still another embodiment of the present invention, the said method shows no adverse effect on the normal growth of the transformed plants.

In further embodiment of the present invention, a novel chimeric Bacillus thuringiensis δ-endotoxin is strategically developed by replacing a polypeptide domain of a δ-endotoxin, herein said Cry1Ea with the corresponding domain of other δ-endotoxins and a novel polypeptide at the C-terminus extreme. A gene is theoretically designed and chemically synthesized to encode the novel chimeric toxin and express it at high level in plant tissue. The gene was expressed in a microbe (E. coli) and two dicot plants (tobacco and cotton).

Efficacy of the strategically designed δ-endotoxin was established in both the systems. The toxicity of the chimeric protein to lepidopteran insect larvae (Spodoptera and Helicoverpa) was improved as compared to the parent proteins. The chimeric synthetic gene is commercially valuable as it can be used to develop agronomically improved crop plants for resistance to insect pests.

In another embodiment of the present invention, accordingly, the present invention provides "a novel δ-endotoxin improved for insecticidal activity and a gene for its high level expression in plants" which comprises strategic designing of a novel chimeric δ-endotoxin, herein said chimeric Cry1E (616 amino acid residues), by replacing a polypeptide domain (from position 530 to 587) of Cry1Ea protein by that of Cry1Ca (from position 533 to 602), incorporation of a novel polypeptide of 25 amino acid residues at the C-terminus extreme, theoretical designing of a gene to code 641 amino acid residue long chimeric δ-endotoxin at a high level in plants, designing and chemical synthesis of oligonucleotides representing theoretically designed gene, assembly of oligonucleotides into double stranded DNA, cloning and sequence analysis of cloned synthetic DNA, construction of vectors for the expression of chimeric gene in E. coli and plants, expression of synthetic chimeric gene in E. coli, comparison of the toxicity of the chimeric protein with the parental proteins against Spodoptera litura and Helicoverpa armigera, transformation of tobacco with the chimeric gene, high level expression of the engineered protein in transgenic plants, purification of chimeric δ-endotoxin protein from transgenic plants and confirmation of its efficacy on larvae of Spodoptera litura and Helicoverpa armigera, evaluation of the potential of the chimeric toxin expressed in transgenic plants for protection against target insect pests.

In an embodiment of the present invention, a naturally occurring δ-endotoxin, namely Cry1Ea has been strategically designed and modified accordingly to make it biologically active against larvae of insect pests, like Spodoptera sp.

In another embodiment of the present invention, 616 amino acid residue long chimeric δ-endotoxin, herein said chimeric Cry1E, was theoretically designed by replacing a peptide domain of Cry1Ea from position 530 to 587 by that of Cry1Ca from position 533 to 602. Further, a novel polypeptide of 25 amino acid residues was introduced at the C-terminus extreme of δ-endotoxin.

In yet another embodiment of the present invention, two peptide domains from positions 530 to 545 and 578 to 587 of Cry1Ea can be replaced by those of Cry1Ca from 533 to 555 and 588 to 602. Such chimeric toxin may also perform similar (or equivalent) biological activity.

In still another embodiment of the present invention, the peptide domain from 530 to 587 of Cry1Ea can be replaced by that of other δ-endotoxins.

In still another embodiment of the present invention, a polypeptide of 25 amino acid residues is introduced at the C-terminus of δ-endotoxin. This polypeptide improved the stability of δ-endotoxin against the proteases of plant. This might have improved the stability of the δ-endotoxin insect mid gut.

In still another embodiment of the present invention, 25 amino acid residues long polypeptide may be included at the C-terminus of other δ-endotoxins, such toxins may become stable against different kind of proteases.

In still another embodiment of present invention, 25 amino acid residues long polypeptide may be incorporated at the C-terminus of any recombinant protein for their stability against proteases.

In still another embodiment of the present invention, a 1.99-kb double stranded DNA was theoretically designed to encode the chimeric protein. Plant preferred codons were used to encode amino acids of the chimeric toxin protein to facilitate high-level expression of the gene in plants.

There are 6 variants of Cry1Aa δ-endotoxin namely Cry1Aa1 to Cry1Aa6 given in EMBL database. Clustal analysis for amino acid sequence of these δ-endotoxin proteins is shown below. At three positions (77, 148 and 302), the amino acid residues are different. The variant positions are shown below in bold letters. However, all six genes have been deployed in toxicity experiments by different laboratories. The efficacy of all six variants in their toxicity towards insects is comparable.

A reference may be cited to Von Tersch et al. 1991, "Insecticidal toxins from *Bacillus thuringensis* subsp *kanyae*: Gene cloning and characterization and comparison with *B. thuringiensis* subsp *kurstaki* Cry1A(c) toxin" in Appl and Environ Microbial, 57: 2: 349-58, wherein two variants of cry1Ac were isolated from two different strains. Their amino acid composition was different at 7 positions. Both the δ-endotoxins were expressed in *E. coli* and toxicity experiment was conducted. The two toxins did not exhibit any difference in efficacy towards target pests.

Further, this clearly states that in proteins, more particularly in the field of endotoxins, the high homology of the sequence is not found to make any significant difference in activity. The above-referred example of endotoxins Cry1Aa1 to Cry1Aa6 clearly reflect the essence of this work. In the instant Application, the applicant has observed extraordinarily high insecticidal activity. Further, the homology of 70% and above in the sequence of chimeric protein Cry1E of the instant Application is also found to show no significant change in the activity. This means that the proteins with sequence homology of 70% and above for chimeric protein Cry 1E are used as insecticidal agents.

In another study (Schnepf et al., 1998, "*Bacillus thuringensis* and its pesticidal crystal proteins", 62: 3, 775-806), amino acid residues GYY of Cry1Ac δ-endotoxin at position 312 to 314 were altered to replace these with ASY, GSY and GFS. No difference in toxicity of the three proteins was noticed.

In addition, there are two natural variants of Cry1C δ-endotoxin namely Cry1Ca and Cry1Cb. These proteins show 81% (Schnepf et al., 1998, "*Bacillus thuringensis* and its pesticidal crystal proteins", 62: 3, 775-806) amino acid sequence identity. Despite this difference, both the toxins are toxic to their target pest, though there is some difference in the level of toxicity. Their host range is also same. (Kalman et al., 1993. "Cloning of a noval cry1C. type gene from a strain of *Bacillus thuringensis* subsp *galleriae*" Appl. Environ Microbial 59: 4: 1131-37)

BRIEF DESCRIPTION OF THE
ACCOMPANYING DRAWINGS

FIG. 1 shows represents PCR based assembly of 58 overlapping oligonuclotides into 1.99 kb novel chimeric cry1E DNA. Lanes 2-4 represent gene assembly in different PCR conditions, the desired DNA fragment is shown with arrow Lane 1 showing λDNA/HindIII-EcoRI molecular weight marker.

FIG. 2 represents the restriction analysis of plasmid pPK59 having E-35-S promoter at the upstream of the novel chimeric gene. The plasmid was digested with SalI restriction enzyme (40 bp downstream of gene). The linear plasmid was further digested with NcoI (lane 2), NheI (lane 3), BstXI (lane 4), NruI (Lane 5) and SacI (lane 6). Lane 1 and 7 represent λDNA/HindIII-EcoRI and λDNA/HindIII molecular weight markers, respectively.

Figure 6:

FIG. 6 represents 100% mortality of $5^{th}$ instar larvae of *Spodoptera* following 48 h of feeding on transgenic tobacco leaf (left). During same period, the larvae fed on control plant leaf ingested 6 leaves (right).

FIGS. 7A-7D are a comparison of six variants of Cry1AA δ-endotoxicity namely: CRY1AA1 (SEQ ID NO:3); CRY1AA2 (SEQ ID NO:4); CRY1AA3 (SEQ ID NO:5); CRY1AA4 (SEQ ID NO:6); CRY1AA5 (SEQ ID NO:7); CRY1AA6 (SEQ ID NO:8).

In still another embodiment of the present invention, 58 oligonucleotides were designed to represent 1.99-kb chimeric cry1E DNA. All oligonucleotides were synthesised chemically and fused enzymatically to obtain desired double stranded DNA. (Please refer FIG. 1)

In still another embodiment of the present invention, two independent constructs were made, each for *E. coli* and plant expression. The parental genes (cry1Ea and cry1Ca) were also introduced in other expression vectors for their expression in *E. coli*.

In still another embodiment of the present invention, all three genes were expressed in *E. coli*. The efficiency of the chimeric Cry1E against *Spodoptera litura* was compared to the parental toxins (Cry1Ea and Cry1Ca). The toxicity experiments established that the engineered toxin is several fold more toxic as compared to the parental proteins.

In still another embodiment of the present invention, the chimeric protein expressed in plants was shown to be also toxic to *Helicoverpa armigera*, another serious insect pest. This established the improvement in the host range of the novel chimeric toxin designed in this study.

In still another embodiment of the present invention, the synthetic gene was introduced in tobacco for expression of the chimeric toxin. The transgenic plants expressed chimeric toxin and accumulated up to 0.5% of total soluble protein. The transgenic plants exhibited excellent protection against larvae of *Spodoptera litura* and caused 100% mortality at all the developmental stages.

In still another embodiment of the present invention, the novel chimeric toxin was purified from total soluble protein from the leaf of the transgenic tobacco plant and mixed in semi synthetic diet. The toxicity experiments again established the efficacy of the hybrid toxin.

The subject invention concerns the discovery of highly active chimeric δ-endotoxins. A novel δ-endotoxin, 641 amino acid residues long, herein said chimeric Cry1E was strategically designed by replacing a polypeptide domain (from position 530 to 587) of Cry1Ea protein by that of Cry1Ca (from position 533 to 602). In this way chimeric toxin comprises amino acid residues 1-529 of Cry1Ea, 530 to 599 of Cry1Ca and 600 to 616 of Cry1Ea. A novel polypeptide of 25 amino acid residues was included as the C-terminus extreme of the δ-endotoxin. In other words, this polypeptide constituted amino acid residue 617-641 of the chimeric toxin.

Several chimeric toxins can be created by replacing different parts of Cry1Ea toxin with strategically designed amino acid sequences or parts of the other toxins. A 1.99 kb nucleotide sequence was theoretically designed to code for the above-mentioned chimeric δ-endotoxin. The gene encoding toxin protein, herein said chimeric cry1E was designed for high-level expression in plants, by introducing plant-preferred codons. The plant preferred codons for each amino acid were distributed evenly to facilitate efficient translation. A translation initiation context appropriate to gene expression in plants (TAAACCATGGCT; (SEQ ID NO:9)) was included at 5' extreme and two translation stop codons (signals) were introduced at the end of the reading frame of the chimeric toxin. A total of 33 unique restriction sites were introduced uniformly throughout the length of the gene at a distance of 40-80 bp. BamHI and HindIII restriction sites were created at the upstream and BamHI and EcoRI at the downstream of the gene to facilitate its cloning. (Please refer FIG. 2).

Figure 1:
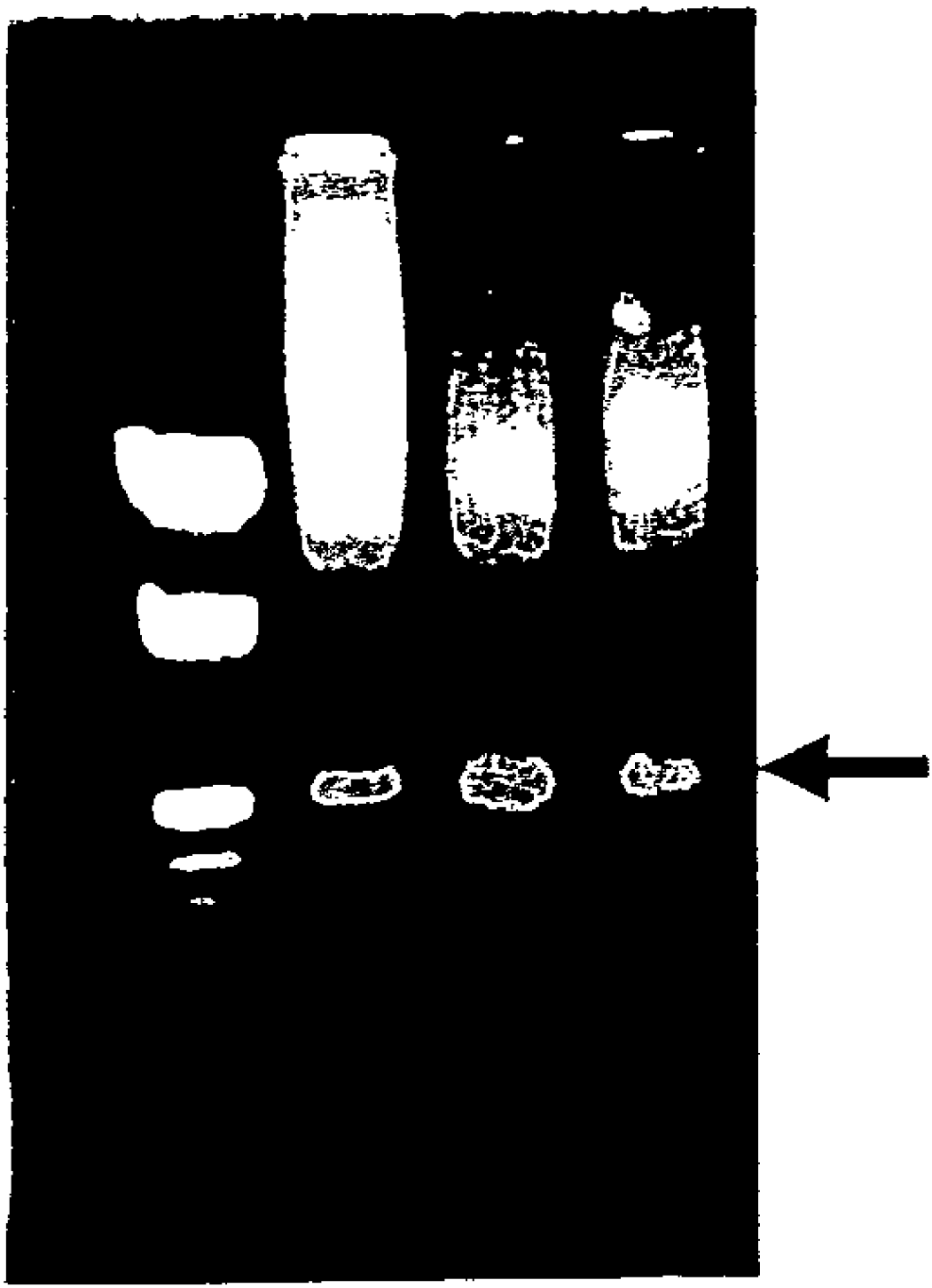

The translation initiation context automatically created an NcoI site at the immediate start of the gene. The gene was divided into 58 overlapping oligonucleotides (40 to 65 nucleotides long) with 6 to 26 base long gaps in between (Please refer FIG. 1). Each oligonucleotide had 13-18 nucleotide long overlap with the immediately adjacent oligonucleotides on the complementary strand. The complementary overlaps were designed to keep $T_m$ value between 48-50° C. The oligonucleotides were synthesised on a DNA synthesiser (Gene Assembler Special, Pharmacia, Sweden) at 200 nmole scale and purified on denaturing urea-PAGE. All 58 oligonucleotides were assembled into 1.99 kb double-stranded DNA, herein said chimeric cry1E gene following the ligation-free gene synthesis method of Singh et al. (1996) and as shown in FIG. 1. The DNA was digested with HindIII and EcoRI restriction enzymes and cloned in pBluescriptII SK(+) (Stratagene, La Jolla, Calif.). The plasmid was named as pPK200. The nucleotide sequence of the synthetic DNA was confirmed by sequencing the cloned synthetic DNA on automated DNA sequencing system (Applied Biosystems model 373A).

A cassette was constructed also for the expression of the chimeric toxin in E.coli under the control of T7lac promoter. The plasmid pPK200 was digested with the restriction enzymes NcoI and BamHI and cloned in expression vector pET-19b (Novagen, Madison Wis.). The plasmid was named as pPK206. DNA encoding Cry1Ca and Cry1Ea toxins were amplified with polymerase chain reaction, using suitable primers, which created NcoI and BamHI restriction sites at the upstream and the downstream of the amplicon. The amplified products were cloned in the pET-19b vector. The constructs having Cry1Ca and Cry1Ea toxin coding DNA were named as pPK135 and pPK141, respectively. E. coli BL21DE3 strain was transformed with the constructs pPK206, pPK135 and pPK141. (Please refer FIG. 3). The toxin proteins were expressed by induction with appropriate concentrations of IPTG. The expression was carried out at 15° C. to avoid possible mis-folding. E. coli cells were lysed with lysozyme and sonicated to release the δ-endotoxins. The toxin proteins were found in inclusion bodies. These were sloubilised in 50 mM Bicarbonate buffer (pH 9.5) at 28° C. The toxin proteins were quantified densitometrically. Serial dilutions of the toxins were mixed in semi-synthetic diet and the mixture was poured in the petri dishes. Total E. coli protein served as control diet. Fifteen neonatal larvae of Spodoptera litura were released onto the cakes of the diet mixture in a 100-ml beaker and the mouth was covered with muslin cloth to allow gas exchange. Each experiment was conducted with 6 replicates. The diet was changed after every alternate day. Bio-assay was conducted with 16/8 h photoperiod at 25±0.2° C. Toxicity data was recorded after 7 days of the feeding. $EC_{50}$ was determined by standard log-probit analysis. All three proteins were tested simultaneously. The representative results are as shown in Table 1 here below.

TABLE 1

| δ-endotoxins(S) | $EC_{50}$ (µg/ml semisynthetic diet) |
|---|---|
| Cry1Ea | >108 |
| Cry1Ca | 29.48 ± 1.77 |
| Chimeric Cry1E | 6.27 ± 0.59 |

The result showed that the E. coli strain expressing the chimeric toxin was several fold more toxic over Cry1Ea and more than four fold toxic over Cry1Ca protein. The Cry1Ea toxin protein failed to cause any effect on the Spodoptera larvae. The result established the successful engineering of the Cry1Ea toxin to develop a novel protein chimeric Cry1E, which is biologically active and an improved toxin. The engineered protein was four fold more toxic than Cry1Ca protein, which is the best-known δ-endotoxin against Spodoptera sp.

All three δ-endotoxins were also tested against 72-h old larvae of Helicoverpa sp. Each larva was released on diet in a separate box. 40 larvae were challenged with each concentration of the toxin. The toxicity results show that the chimeric toxin is also toxic to Helicoverpa. A representative result is shown in Table 2 as here below.

TABLE 2

| δ-endotoxins(S) | $EC_{50}$ (µg/ml semisynthetic diet) |
|---|---|
| Cry1Ea | >176 |
| Cry1Ca | 136.22 ± 8.77 |
| Chimeric Cry1E | 26.71 ± 1.39 |

As used here, reference to the "toxin" means, the N-terminal segment, which is responsible for the insect pesticidal activity. A person skilled in this art can convert this toxin into a protoxin by including a part or complete C-terminus fragment of a homologous or hetrologous δ-endotoxin. Such protoxin will be a very stable molecule inside a microbial cells for example, in E. coli, Pseudomonas etc. and can be used in developing microbial formulations. Such formulations can be used as pesticides. Development of such protoxins and formulations using the novel toxin developed by us is also within the scope of the invention claimed by us.

The gene and toxin useful according to the subject invention include not only 641 amino acid long toxin but also fragments of the novel sequence, variants and mutants, which retain the characteristic pesticidal activity of the toxin specifically exemplified herein. As used here, the terms "variants" or "variations" of genes refer to nucleotide sequences, which encode the same toxins or which encode toxins having lower or equivalent pesticidal activity. As used here, the term "equivalent pesticidal activity" refers to toxins having similar or essentially the same biological activity against the target pests as the claimed toxins.

It is well within the skill of a person trained in the art to create alterative DNA sequences encoding the same or essentially the same, toxin. These variant DNA sequences are within the scope of the subject invention. As used herein, reference to "essentially the same" sequence refers to sequences, which have amino acid substitutions, deletions, additions or insertions, which do not materially affect pesticidal activity. Fragments retaining pesticidal activity are also included in this definition.

A novel chimeric toxin of the subject invention has been specifically exemplified herein. It should be readily apparent that the subject invention comprises variants or equivalent toxins (and nucleotide sequences encoding equivalent toxins) having the same or similar pesticidal activity of the exemplified toxin. Equivalent toxins will have amino acid homology with the exemplified toxin. This amino acid homology will typically be greater than 75%, preferably be greater than 90% and most preferably be greater than 95%. The amino acid homology will be highest in critical regions of the toxin, which account for the biological activity or are involved in the determination of three-dimensional configuration, which ultimately is responsible for the biological activity. In this regard, certain amino acid substitutions are acceptable and can be expected if these substitutions are in regions, which are not critical in biological activity or are conservative amino acid substitutions, which do not affect the three-dimensional configuration of the molecule. For example, amino acids may be placed in the following classes: non-polar, uncharged polar, basic and acidic. Conservative substitutions whereby an amino acid of one class is replaced with another amino acid of the same class fall within the scope of the subject invention so long as the substitution does not materially alter the biological activity of the δ-endotoxin. Table 3 as given here below provides a listing of examples of amino acids belonging to each class.

TABLE 3

| Class of Amino Acid | Examples of Amino Acids |
| --- | --- |
| Non-polar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin. It is well within the skill of a person trained in the art of protein engineering to substitute any amino acid of the chimeric toxin with alanine. The substitution of any amino acid is safest, as alanine is a typical amino acid. Such substitution is also well within the scope of the invention.

A gene encoding the chimeric toxin of the subject invention can be introduced into a wide variety of microbial or plant hosts. Expression of the toxin gene results, directly or indirectly, in the intracellular production and maintenance of the pesticidal chimeric toxin. With suitable microbial hosts, e.g., *Pseudomonas*, the microbes can be applied to the sites where the pests proliferate. This will result into the control of the pest. Alternatively, the microbe hosting the toxin gene can be treated under conditions that prolong the activity of the toxin and stabilize the cell. The treated cell, which retains the toxic activity, then can be applied to the environment of the target pest: Where the gene encoding the chimeric toxin is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes;* fungi, particularly yeast, e.g., genera *Saccharomyces, Cryptococcus, Kluyveromyces, Sporobolomyces, Rhodotorula* and *Aureobasidium*. Of the particular interest are such phytosphere bacterial species as *Pseudomonas syringae, Pseudomonas fluorescens, Serratia marcescens, Acetobacter xylinum, Agrobacterium tumefaciens, Rhodopseudomonas spheroids, Xanthomonas campestris, Rhozobium melioti, Alcaligenes entrophus* and *Azotobacter vinlandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae* and *Aureobasidium pollulans*. of particular interest are the pigmented microorganisms. A wide variety of ways are available for introducing a gene encoding a chimeric toxin into a microorganism host under conditions, which allow for the stable maintenance and expression of the gene. These methods are well known to those skilled in the art and are described, for example, in U.S. Pat. No. 5,135,867, which is incorporated herein by reference.

Figure 2:
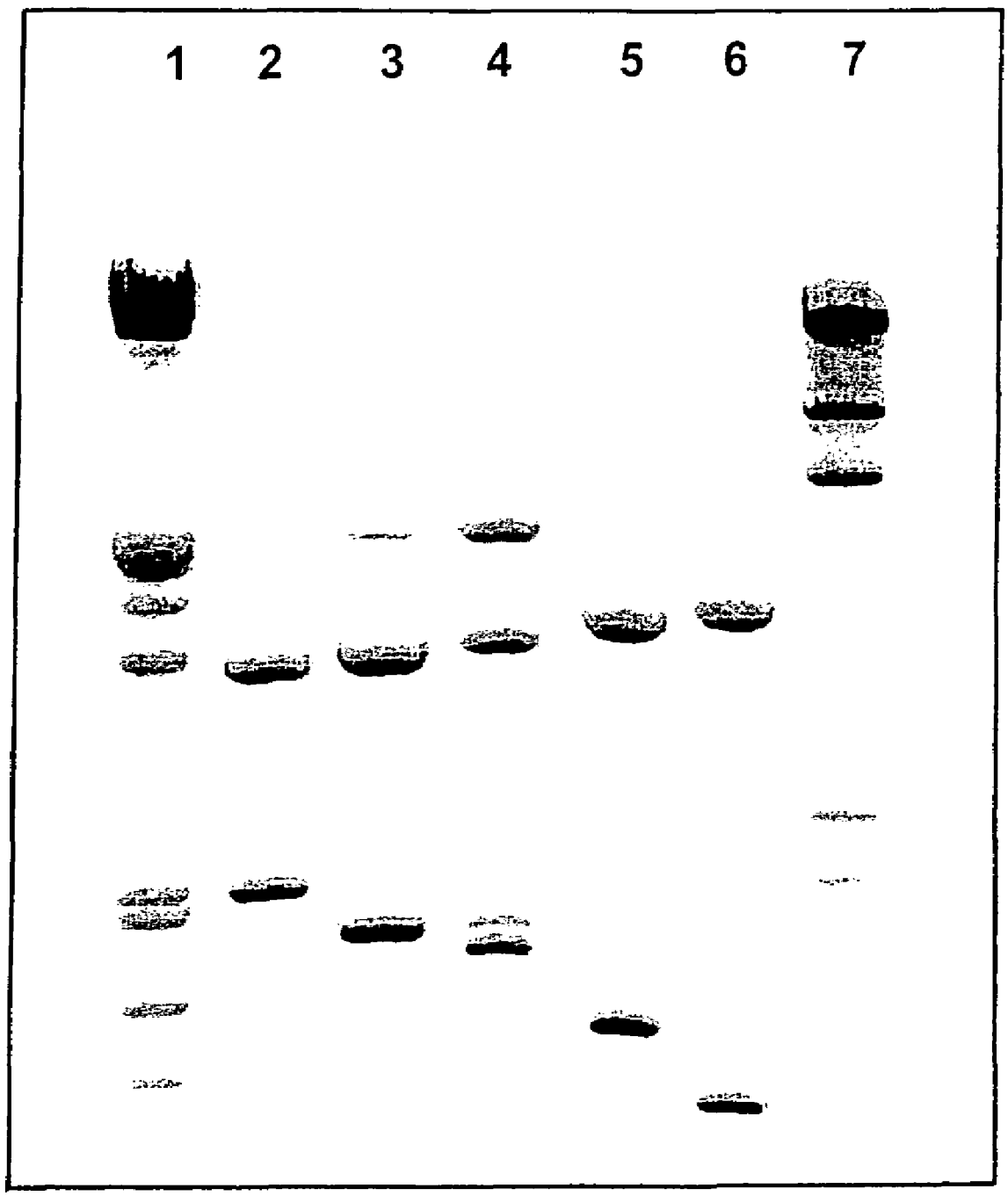
Figure 3:
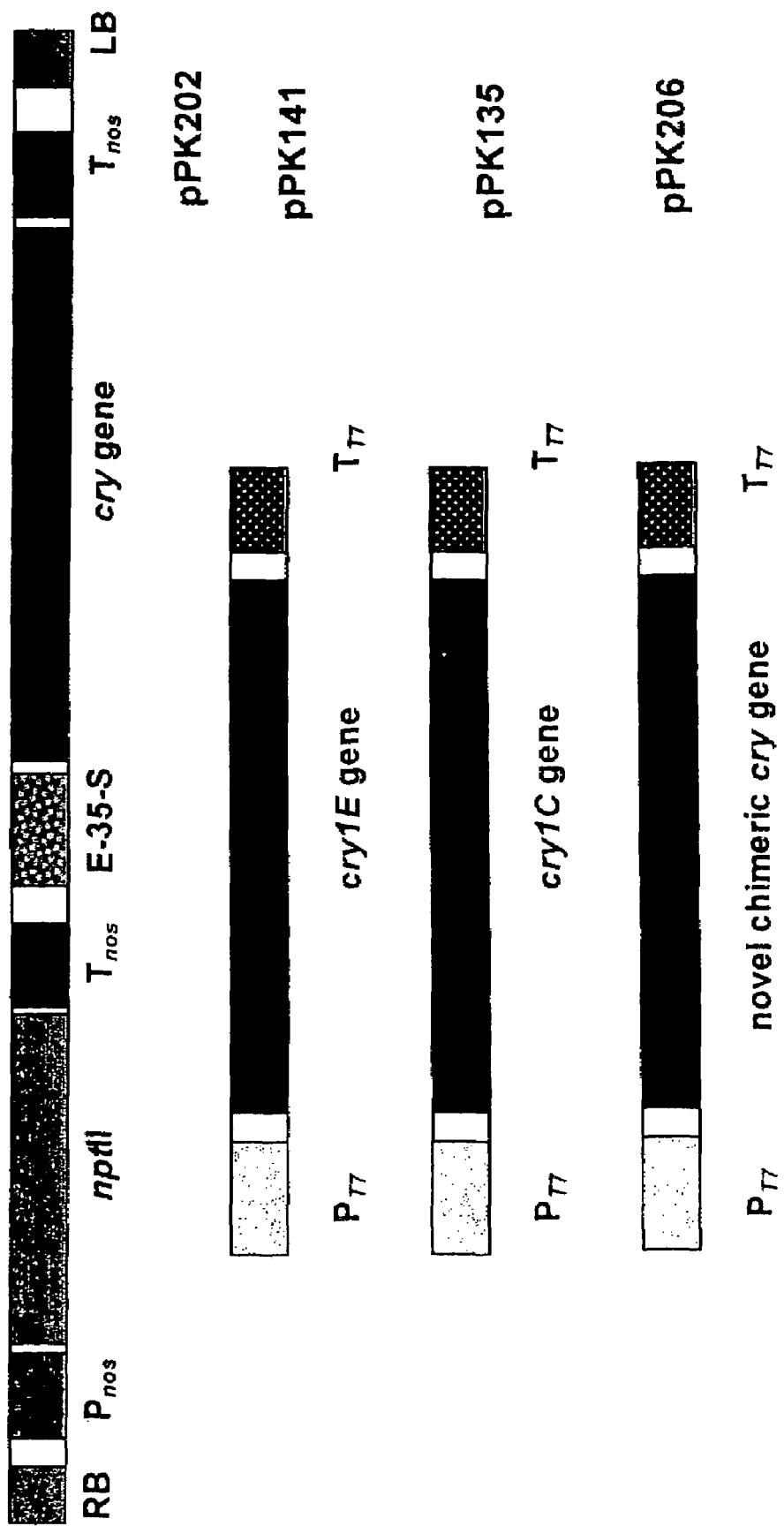
FIG. 3 represent map of plasmids pPK202, pPK141, pPK135 and pPk206.

A plant transformation vector was constructed for the development of transgenic plants. A plasmid pPK58 (having CaMV35S promoter with duplicated enhancer) was digested with BamHI and HindIII and pPK200 with HindIII and EcoRI to excise out CaMV35S promoter with the duplicated enhancer and chimeric cry1E gene, respectively. A triple ligation was carried for cloning of the two fragments in pLIT-MUS38 cloning vector (New England Biolabs). The plasmid, namely pPK59 had CaMV35S promoter with the duplicated enhancer at the upstream of the chimeric gene. Restriction analysis of pPK59 is shown in FIG. 2. The nos transcription terminator was cloned at the downstream of the chimeric gene. DNA of nos polyadenylation element was amplified using pBI101.1 as template with suitable primers, which created MfeI and EcoRI restriction sites at the upstream and downstream, respectively. The plasmid pPK59 was digested with EcoRI and the PCR product was cloned following digestion with the MfeI and EcoRI restriction enzymes. The clone in which EcoRI restriction site of the synthetic gene was ligated to MfeI site of nos terminator (as they have compatible ends), selected and named as pPK201. The correct orientation of nos terminator was confirmed by restriction analysis and also by sequencing. The expression cassette (the synthetic cry gene with E-35S promoter and nos terminator) was cloned in Ti binary vector. BamHI-EcoRI fragment of plasmid pPK201 was cloned in pBI101.1 replacing BamHI-EcoRI fragment (uidA gene and nos terminator) of the plasmid. This binary vector was named as pPK202. The map of the *E. coli* and plant expression vectors are shown in FIG. 3.

In order to study the efficacy of the chimeric Cry1E toxin in plants, tobacco was selected for the expression. *Agrobacterium tumefaciens* strain LBA 4404 containing the helper plasmid pAL4404 was transformed with the binary vector pPK202 following the modified protocol of "electroporation of *Agrobacterium*" discussed by Cangelosi et al. (1991) and transformed colony was selected on antibiotics streptomycin, rifampicin and Kanamycin8. *Agrobacterium* mediated transformation of *Nicotiana tobacum* cv. Patit Havana was carried out following the method of Horsch et al., 1985 and the transgenic plant were selected on the antibiotic kanamycin. The presence of the gene encoding chimeric toxin was confirmed with PCR and Southern analysis and the expression of the transgene was established with the RT-PCR, Western analysis and ELISA. ELISA result displayed 0.5% expression of the toxin protein out of total soluble leaf protein in a selected transgenic line. This high level of the expression was the result of the designing of the gene in which plant-preferred codons were exclusively used. Plant preferred translation initiation context used in this study would also have played an important role in achieving enhanced expression.

Figure 4:
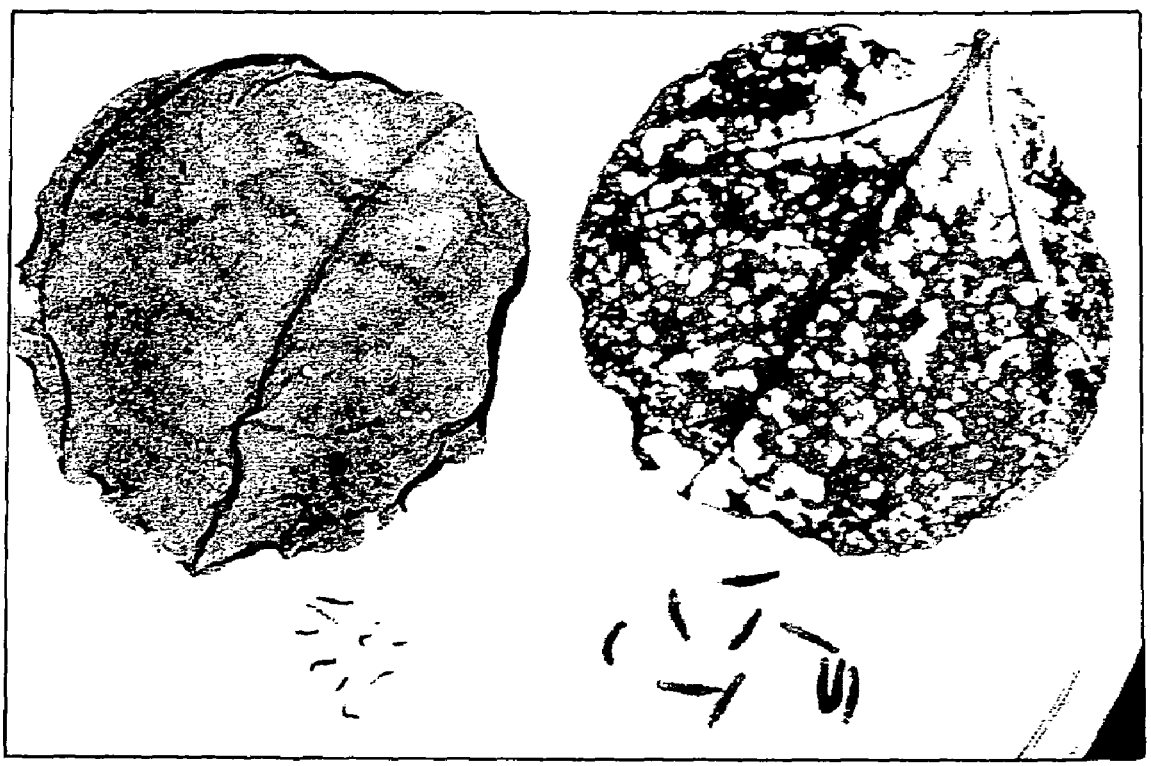
FIG. 4 represents insect bioassay with transgenic tobacco plants. $1^{st}$ instar larvae of *Spodoptera litura* showing 100% mortality after 2 days of feeding on transgenic leaf expressing the novel chimeric cry1E gene (left). Control leaf was eaten by larvae voraciously (right).
Figure 5:
FIG. 5 represents $3^{rd}$ instar larvae of *Spodoptera litura* showing 100% mortality after 2 days of feeding (left). Transgenic plant leaf exhibited high level of protection against larvae in contrast to the control plant leaf (right).

Insect bioassay was performed with two months old transgenic plants and $1^{st}$ and $5^{th}$ instar larvae of *Spodoptera litura*. (Please refer FIGS. 4-6). 15 cm² leaf-discs of transgenic and control plants were placed in cylindrical boxes containing wet blotting paper at the bottom and ten $1^{st}$ instar larvae were released onto them. Mouths of the boxes were covered with wet muslin cloth to maintain sufficient humidity and exchange of air. The toxicity experiments were conducted in three replicates at 25±0.2° C. and 16/8 h photoperiod was maintained. In bioassay with $5^{th}$ instar larvae, complete leaves of transgenic and control plants were used. The leaf petiole was held in cotton plug over a 250 ml flask containing ½ MS salt solution to overcome wilting of the leaf. Five insect larvae were allowed to feed on each leaf. The leaves of control plant were changed after every 8 h and they were consumed completely by the insect larvae.

The result (FIGS. 4 and 6) established that $1^{st}$ as well as $5^{th}$ instar larvae died within 48-72 h. The amount of leaf eaten by the $1^{st}$ instar larvae was negligible as compare to the control plant leaf discs, which were eaten voraciously. Ingestion of approximately 1 cm² of transgenic leaf was sufficient to kill $5^{th}$ instar larvae. These larvae appeared moribund after 8-16 h of feeding on the transgenic leaf and finally died within 2-3 days. Green coloured excreta with high water content were noticed on leaf surface. Some of the larvae showed heavy weight loss before death. In a separate experiment, different instar larvae were allowed to feed on leaves of transgenic plant for 1 h, 2 h, 4 h, 8 h and 16 h and then shifted to control plant leaves. It was observed that 8 h of feeding on transgenic plants was sufficient to cause 100% mortality of larvae in all stages of development, even after feeding on non-transgenic plants. Ingestion of very small amounts of the toxin by young larvae delayed their pupation by 10-15 days from normal larval cycle of 15 days. The few larvae that escaped mortality developed into flies. 40% of the paired matings where such flies were used, gave eggs. However, the eggs were sterile and failed to hatch. The total soluble protein from transgenic tobacco plant was extracted and loaded on SepharoseQ ion exchange column. The protein was eluted with increasing gradient of sodium chloride and the peak containing δ-endotoxin was pooled and desalted on G10 column. The eluted protein was mixed in semi-synthetic diet. Similar protein extraction and purification from the leaf of non-transgenic tobacco plants was also performed and such plant protein served as control. The toxicity experiment was conducted as discussed earlier. $EC_{50}$ for *Spodoptera litura* and *Helicoverpa armigera* was 37 ng/ml and 285 ng/ml of artificial diet. The result again confirmed the efficacy of chimeric δ-endotoxin towards target insect pests.

A novel δ-endotoxin for the control of insect pests and a gene for its high level expression in plants, which comprises theoretical designing of a novel δ-endotoxin, herein named chimeric Cry1E, strategically designed by replacing a polypeptide domain (from position 530 to 587) of Cry1Ea protein by that of Cry1Ca (from position 533 to 602), a novel 25 amino acid residues long polypeptide at the C-terminus extreme of the protein for stability, theoretical designing of the gene to express the chimeric δ-endotoxin at a high level in plants, designing and chemical synthesis of the oligonucleotides representing the theoretically designed gene, assembly of oligonucleotides into double stranded DNA, cloning and sequence analyses of the cloned synthetic DNA, construction of vectors for the expression of chimeric gene in *E. coli* and plants, expression of the synthetic gene in *E. coli*, comparison of the toxicity of the chimeric protein with the parental proteins against *Spodoptera litura*, transformation of plant, for example tobacco with the chimeric gene, high level expression of the engineered protein in transgenic plants and evaluation of the potential of the chimeric toxin in transgenic plants for protection against *Spodoptera litura*.

In still another embodiment of the present invention, wherein amino acid no. 1 to 529 of Cry1Ea, 530 to 599 of Cry1Ca, 600 to 616 of Cry1Ea and 617 to 641 a novel polypeptide and its structurally and/or functionally equivalent variants or fragments thereof.

In still another embodiment of the present invention, wherein the said toxin has an amino acid sequence shown in SEQ ID No.1; shows several fold higher toxicity to target lepidopterin insects as compared to the parental toxins Cry1Ea and Cry1Ca.

In still another embodiment of the present invention, wherein chimeric cry1E gene which encodes a chimeric toxin having activity against lepidopteran insects, has nucleotide sequence shown in SEQ ID No 2 or its fragment thereof.

In still another embodiment of the present invention, wherein a process of controlling lepidopteran pests employing the protein, with an effective amount of the toxin used as such or as a component of a chemical or microbial formulation.

In still another embodiment of the present invention, wherein a recombinant DNA transfer vector comprising a polynucleotide sequence, which encodes a toxin having activity against lepidopteran insects, wherein said polynucleotide sequence has the nucleotide sequence of SEQ ID NO. 2 or fragments thereof.

In still another embodiment of the present invention, wherein a recombinant host transformed with the gene.

In still another embodiment of the present invention, wherein the said host is a microbe for example *Escherichia coli, Pseudomonas*, Yeast, Cyanobacteria and/or other microbes.

In still another embodiment of the present invention, wherein said transformed host is a plant for example tobacco, cotton, chickpea, pegeonpea, groundnut, cauliflower, cabbage, chilli, capsicum and/or other plants, which expresses the toxin, wherein said toxin has the amino acid sequence of SEQ ID NO. 1, or its variants with equivalent activity against lepidopteran insects.

In further embodiment of the present invention, instant Application clearly states that in proteins, more particularly in the field of endotoxins, the high homology of the sequence is not found to make any significant difference in activity. The above-referred work on of endotoxins Cry1Aa1 to Cry1Aa6 clearly reflect the essence of this work. In the instant Application, the applicant has observed extraordinarily high insecticidal activity. Further, the homology of 70% and above in the sequence of chimeric protein Cry1E of the instant Application is also found to show no significant change in the activity. This means that the proteins with sequence homology of 70% and above for chimeric protein Cry 1E are used as insecticidal agents.

The following examples are given by way of illustrations and therefore should not be construed to limit the scope of the present invention.

EXAMPLE 1

Comparative Toxicity of the Novel Chimeric Cry1E Expressed in *E. coli* to Larvae of Lepidopteran Insect Pests A chimeric δ-endotoxin, 616 amino acid residues long, herein said chimeric Cry1E was strategically designed by replacing a polypeptide domain (from position 530 to 587) of Cry1Ea protein by that of Cry1Ca (from position 533 to 602). A polypeptide of 25 amino acid residues was additionally included at the C-terminus extreme as described earlier. A 1.99 kb nucleotide sequence was theoretically designed to code for the above-mentioned chimeric δ-endotoxin. The codons for each amino acid were distributed evenly to avoid temporary deficiency of the tRNA during translation. Several δ-base cutter restriction enzyme sites were created in the designed gene. BamHI, HindIII and NcoI restriction sites were created at 5'-end and EcoRI at the 3'-end of the designed gene. The gene was divided into 58 overlapping oligonucleotides (40 to 65 nucleotides long). Each oligonucleotide had 13-18 nucleotide long overlap with the immediately adjacent oligonucleotides on the complementary strand ($T_m$ between 48-50° C.). Oligonucleotides were synthesised on a DNA synthesiser (Gene Assembler Special, Pharmacia, Sweden) at 200 nmole scale and purified on denaturing urea-PAGE. All 58 oligonucleotides were assembled into the double-stranded DNA, herein said chimeric cry1E gene following the ligation-free gene synthesis method of Singh el al. (1996) and as shown in FIG. 1. The DNA was digested with HindIII and EcoRI restriction enzyme and cloned in pBluescriptII SK(+) (Stratagene). The plasmid was named as pPK200. The nucleotide sequence of the synthetic DNA was confirmed by sequencing of the cloned synthetic DNA on automated DNA sequencing system (Applied Biosystems model 373).

A cassette was constructed for the expression of the chimeric toxin in *E.coli* under control of T7 promoter. For this, plasmid pPK200 was digested with the restriction enzymes NcoI and BamHI and cloned in expression vector pET-19b (Novagen). The plasmid was named as pPK206. DNA encoding toxin portion of Cry1Ea and Cry1Ca were amplified with polymerase chain reaction, using suitable primers, which created NcoI and BamHI restriction sites at the upstream and the downstream of the amplicon, respectively in both the DNA. The amplified products were cloned at NcoI and BamHI sites in the same vector (pET-19b). The constructs having Cry1Ea toxin DNA was named as pPK141 and Cry1Ca as pPK135 as described earlier. BL21DE3 strain of *E. coli* was transformed with the constructs pPK141, pPK135 and pPK206. The toxin proteins were expressed by induction with appropriate concentrations of IPTG. The expression was carried out at 15° C. to avoid any possible mis-folding of the toxins. The toxin proteins were quantified densitometrically on the denaturing polyacrylamide gel. Serial dilutions of the toxins were mixed in semi-synthetic diet. Total *E. coli* protein served as control in the diet. Fifteen neonatal larvae of *Spodoptera litura* were released onto the cakes of the diet mixture in a 100-ml beaker and the mouth of the beaker was covered with muslin cloth to allow gas exchange. Each experiment was conducted in 6 replicates. The diet was changed after every alternate day. Bio-assay was conducted with 16/8 h photoperiod at 25±0.2° C. Toxicity data was recorded after 7 days of the feeding. $EC_{50}$ was determined by standard log-probit analysis. All three proteins were tested simultaneously. The representative results are presented in Table 4 as given here below.

TABLE 4

| δ-endotoxins(S) | $EC_{50}$ (µg/ml semisynthetic diet) |
|---|---|
| Cry1Ea | >108 |
| Cry1Ca | 29.48 ± 1.77 |
| Chimeric Cry1E | 6.27 ± 0.59 |

The result showed that the chimeric toxin was several fold more toxic over Cry1Ea and more than four fold toxic over Cry1Ca protein. Cry1Ea toxin protein failed to cause any mortality or growth retardation of the *Spodoptera* larvae. The result established the successful engineering of the Cry1Ea toxin for converting it into a biologically active improved toxin. The engineered protein was more toxic than Cry1Ca protein, which is the best-known δ-endotoxoin against *Spodoptera* sp.

A similar toxicity experiment was conducted with the larvae of *Helicoverpa armigera*. In this case, 72 h old larvae were released on semi-synthetic diet containing one of the three proteins and only one larvae was released in each box. Weight loss was recorded after 7 days of feeding. The representative results are presented in Table 5 as shown here below.

TABLE 5

| δ-endotoxins(S) | $EC_{50}$ (µg/ml semisynthetic diet) |
|---|---|
| Cry1Ea | >176 |
| Cry1Ca | 136.22 ± 8.77 |
| Chimeric Cry1E | 26.71 ± 1.39 |

The result shows that the novel chimeric δ-endotoxoin designed by us is not only more toxic to *Spodoptera* but also effective against *Helicoverpa*. The designing has widened the host range of the toxin as well as substantially improved toxicity over the parental proteins.

EXAMPLE 2

High Larval Toxicity of the Transgenic Plants Expressing Novel Chimeric Cry1E Protein In order to establish efficacy of the novel chimeric toxin in plants, a plant transformation vector was constructed for the development of transgenic plants. A plasmid pPK58 (having CaMV35S promoter with duplicated enhancer) was digested with BamHI and HindIII and pPK200 with HindIII and EcoRI to excise out CaMV35S promoter with the duplicated enhancer and chimeric cry1E gene, respectively. A triple ligation was carried for the cloning of the two fragments in pLITMUS38 cloning vector (New England Biolabs). The plasmid was named pPK59, which had CaMV35S promoter with the duplicated enhancer at the upstream of the chimeric gene. The nos transcription terminator was cloned at the downstream of the chimeric gene nos polyadenylation element was amplified using pBI101.1 as template with suitable primers, which created MfeI and EcoRI restriction sites at the upstream and downstream, respectively. The plasmid pPK59 was digested with EcoRI and the PCR product was cloned following the digestion with the MfeI and EcoRI restriction enzymes. The clone in which EcoRI restriction site of the synthetic gene ligated to MfeI site of nos terminator (as they have compatible ends) was selected and named as pPK201.

The correct orientation of nos terminator was confirmed by restriction analysis and also by DNA sequencing. The expression cassette (the synthetic cry gene with E-35S promoter and nos terminator) was cloned in Ti binary vector. BamHI-EcoRI fragment of plasmid pPK201 was cloned in pBI101.1 replacing BamHI-EcoRI fragment (uidA gene and nos terminator) of the plasmid. This binary vector was named as pPK202. The construction of *E. coli* and plant expression vector is schematically presented in FIG. 3. The construct had polynucleotide sequences TAAACCATG GCT (SEQ ID NO:9) as plant preferred translation initiation context, TAA TGA were introduced in synthetic gene for translational termination. *Agrobacterium tumefaciens* strain LBA 4404 containing helper plasmid pAL4404 was transformed with binary vector pPK202 following the modified protocol of "electroporation of *Agrobacterium*" discussed by Cangelosi et al. (1991) and transformed colony was selected on antibiotics streptomycin, rifampicin and kanamycin. *Agrobacterium* mediated transformation of *Nicotiana tabacum* cv. Patit Havana was carried out following the method of Horsch et al., 1985 and the transgenic plant were selected on the antibiotic kanamycin. The presence of the gene encoding chimeric toxin was confirmed with the PCR and Southern Analysis and the expression of the transgene was established with the RT-PCR, Western analysis and ELISA. ELISA result established 0.5% expression of the toxin protein in total soluble leaf protein in the transgenic line selected for these experiments. This high level of the expression was the result of the designing of the gene in which plant-preferred codons were exclusively used. Plant preferred translation initiation context also would have played an important role in the expression. Insect bioassay was performed with the leaves of two-month-old transgenic plants and neonatal larvae of *Spodoptera litura*. 15 cm² leaf-discs of transgenic and control plants were placed in cylindrical boxes containing wet blotting paper at the bottom and ten $1^{st}$ instar larvae were released onto them. Mouths of the boxes were covered with wet muslin cloth to maintain sufficient humidity and to allow the exchange of air. The toxicity experiments were conducted in six replicates at 25±0.2° C. and 16/8 h photoperiod was maintained. The result showed (FIG. 4) that the transgenic plants expressing novel chimeric protein were highly toxic to the neonatal larvae of *Spodoptera litura* and cause 100% mortality within 48 h of feeding. The damage of leaf-discs by the insect larvae was negligible as compared to control plant leaf-discs, which were almost completely eaten away. High level of the protection of the transgenic plant and mortality of *Spodoptera* larvae upon feeding on transgenic plants again established the efficacy of the chimeric toxin and the transgenic plants.

EXAMPLE 3

High Toxicity of the Chimeric Cry1E Protein to Larvae of *Spodoptera* sp. in all the Stages of Their Development A bioassay was conducted on $1^{st}$ (3 days old), $3^{rd}$ (7 days old) and $5^{th}$ (12 days old) instar larvae to established the efficacy of the engineered protein expressed in the transgenic plants. Bioassay with $1^{st}$ instar larvae has been discussed in example 2. Complete leaves of transgenic and control plants were used for feeding the advanced stage larvae. The leaf petiole was held in cotton plug over a 250 ml flask containing ½ MS salt solution to overcome wilting of the leaf. 5 insect larvae were allowed to feed on each leaf. The leaves of control plant fed by $3^{rd}$ (FIG. 5) and $5^{th}$ (FIG. 6) instar larvae were changed after 16 h and 8 h, respectively, as they were consumed completely by the insect larvae. The result established that feeding on transgenic leaf causes mortality of larvae in all the developmental stages within 48 h. Ingestion of approximately 1 cm² of transgenic leaf was sufficient to kill $5^{th}$ instar larvae. These larvae appeared moribund after 8-16 h of feeding on the transgenic leaf and finally died within 2 days. Green coloured excreta with high water content were noticed on leaf surface. Some of the larvae showed heavy weight loss before death.

In a separate experiment, different instar larvae were fed on leaves of transgenic plants for 1 h, 2 h, 4 h, 8 h and 16 h and then shifted to control plant leaves. It was observed that 4 h of feeding on transgenic plants was sufficient to cause 100% mortality of larvae in all stages of development, even when they were subsequently fed on non-transgenic plants. Ingestion of very small amounts of the toxin by young larvae delayed their pupation by 10-15 days beyond the normal larval cycle of 15 days. The few larvae that escaped mortality developed into flies. 40% of the paired matings using such flies gave eggs. However, the eggs were sterile and failed to hatch. The toxicity of δ-endotoxin to advance stage insect larvae has not been reported in literature till date. The high level of toxicity may be due to higher stability of chimeric toxin in the mid gut of insect larvae or improved receptor binding and pore-forming ability of δ-endotoxin. The example again established the potential of the chimeric toxin against *Spodoptera* sp. Since *Helicoverpa* does not prefer to eat tobacco leaf, toxicity experiment with transgenic tobacco plants could not be conducted on *Helicoverpa*.

EXAMPLE 4

High Toxicity of the Novel Chimeric Cry1E Prepared from Leaves of Transgenic Tobacco Plants Expressing δ-Endotoxin Total soluble protein was prepared from leaves of transgenic tobacco. Fresh leaf tissue was powered under liquid $N_2$ and then suspended in 5 volumes of protein extraction buffer (TrisCl, 20 mM, pH 9.5; EDTA 2 mM, pH 8.0; NaCl, 50 mM; DTT, 1 mM; PVP 2% and PMSF, 100 mM). The suspension was mixed well and centrifuged twice (20,000×g, 20 min and 4° C.). The supernatant was loaded on Sepharose Q column (10 cm×2.5 cm). The protein was eluted with increasing gradient of NaCl in extraction buffer and 100 fractions of 5 ml were collected. The δ-endotoxin was detected with ELISA. The fractions containing the δ-endotoxin were pooled. A known amount of the plant-purified δ-endotoxin was mixed in semi-synthetic diet. The toxicity trials were conducted with 3-day old larvae of *Spodoptera litura* and *Helicoverpa armigera*, as described in previous examples. The result showed that $EC_{50}$ (the concentration required for 50% killing) for *Spodoptera* and *Helicoverpa* were 42.39±1.72 ng/ml and 283.11±8.29 ng/ml of semi-synthetic diet. The result further established the high level of toxicity to the larvae of *Spodoptera* and *Helicoverpa*. The point is noteworthy that insecticidal crystal protein made in plant tissue is much more toxic as compared to the same protein made in *E. coli*. Probably the δ-endotoxin folds much better in plant cytoplasm, the role of some unidentified chaperons in such folding cannot be overruled.

EXAMPLE 5

Stability of Chimeric δ-Endotoxin in Plant Tissue

Total soluble leaf protein of transgenic plant was extracted as discussed earlier and incubated at 4° C. and 28° C. They were used for toxicity trials. The samples were taken out after every two days in case of former and every day in case of later.

The total crude protein was mixed in semi synthetic diet and toxicity experiment was carried out with neonatal larvae of *Spodoptera litura*. The insect mortality data was recorded after 7 days of feeding and $LC_{50}$ was calculated. The results are shown in Tables 6, and 7 here below.

TABLE 6

| S.No. | Incubation period of crude protein at 4° C. (in days) | $LD_{50}$ (in ng/ml of semi-synthetic diet) |
|---|---|---|
| 1. | 2 | 48.71 ± 2.4 |
| 2. | 4 | 57.87 ± 2.96 |
| 3. | 6 | 66.44 ± 3.65 |
| 4. | 8 | 70.19 ± 3.55 |
| 5. | 12 | 73.82 ± 3.1 |
| 6. | 16 | 74.37 ± 3.67 |

TABLE 7

| S.No. | Incubation period of crude protein at 28° C. (in days) | $LD_{50}$ (in ng/ml of semi-synthetic diet) |
|---|---|---|
| 1. | 1 | 76.44 ± 3.3 |
| 2. | 2 | 98.13 ± 4.6 |
| 3. | 3 | 143.46 ± 8.5 |
| 4. | 4 | — |
| 5. | 5 | — |

The result established the stability of chimeric δ-endotoxin designed by us against the plant proteases. The chimeric toxin was stable for more than 16 days at 4° C. and 3 days at 28° C., and caused more than 80% mortality. Increase in $LC_{50}$ with time was presumably due to some degradation of the toxin.

Main advantages of the present invention are:
1. Cry1Ea δ-endotoxin was engineered to obtain a novel chimeric toxin, herein said chimeric Cry1E. The toxicity of the chimeric protein was several fold higher as compared to the parent toxins or other δ-endotoxin reported to function against *Spodoptera*. Its larvicidal activity was very high when it is made in plants.
2. The gene encoding chimeric toxin was designed to express both in *E. coli* and plants. Hence, it can be used in the engineering of a microbe for the expression of chimeric toxin, which can be used in the preparation of the microbial formulation. The same gene can also be used in the genetic engineering of the plants for the trade of insect resistance. We have shown that the sequence designed by us gives very high level of expression (0.5% of the total soluble protein) of the chimeric toxin in transgenic tobacco and cotton leaves (results not included).
3. The transgenic plants expressing the chimeric toxin exhibited very high degree of protection against the larvae of *Spodoptera litura* in all developmental stages. They died within 2-3 days of feeding on the transgenic plants. Such high level of toxicity of transgenic plants against any lepidopteran insect has not been reported till date. This protein may also be effective against many other insect larvae. Our results show that the toxin was effective against *Helicoverpa* also.
4. Potential of the chimeric toxin in transgenic plants was further established by short-term feeding on transgenic plants. Feeding for 4 hours caused 100% mortality of *Spodoptera* larvae at all the developmental stages. The feeding for extremely short (up to one hour) periods, delayed larval development and interfered with metamorphosis. Such protein may be extremely valuable in protecting agronomically important crops and forests. The gene coding chimeric toxin can be used in the development of transgenic plants and/or for production of the toxin in a microbe, which can be used in microbial formulations.
5. Since the transgenic plants expressing the novel chimeric toxin caused 100% mortality of *Spodoptera* larvae within a very short period of feeding, the probability of the development of resistance in insects against this δ-endotoxin will be extremely low.

The invention claimed is:

1. A protein comprising amino acids 1-641 in SEQ ID NO:1.

* * * * *

UNITED STATES PATENT AND TRADEMARK OFFICE
CERTIFICATE OF CORRECTION

PATENT NO. : 7,557,186 B2
APPLICATION NO. : 11/062225
DATED : July 7, 2009
INVENTOR(S) : Rakesh Tuli It is certified that error appears in the above-identified patent and that said Letters Patent is hereby corrected as shown below:

Cover Page, (56) References Cited, OTHER PUBLICATIONS, col. 1, line 11, "Lepidoperan" should be -- Lepidopteran --.

Cover page, (56) References Cited, OTHER PUBLICATIONS, col. 2, line 37, "an" should be -- and --.

Cover page, (56) References Cited, OTHER PUBLICATIONS, col. 2, line 44, "Baciluus" should be -- Bacillus --.

Column 49, line 63, "NO:1" should be -- NO: 1 --.

Signed and Sealed this

Twenty-ninth Day of September, 2009

David J. Kappos
*Director of the United States Patent and Trademark Office*